United States Patent
Handique et al.

(10) Patent No.: US 10,345,219 B2
(45) Date of Patent: Jul. 9, 2019

(54) CELL CAPTURE SYSTEM AND METHOD OF USE

(71) Applicant: DeNovo Sciences, Inc., Plymouth, MI (US)

(72) Inventors: Kalyan Handique, Plymouth, MI (US); Priyadarshini Gogoi, Plymouth, MI (US); Christopher Siemer, Plymouth, CA (US); Saedeh Sepehri Javdani, Plymouth, MI (US)

(73) Assignee: Celsee Diagnostics, Inc., Plymouth, MI (US)

( * ) Notice: Subject to any disclaimer, the term of this patent is extended or adjusted under 35 U.S.C. 154(b) by 144 days.

(21) Appl. No.: 15/657,553

(22) Filed: Jul. 24, 2017

(65) Prior Publication Data

US 2017/0322142 A1 Nov. 9, 2017

Related U.S. Application Data

(63) Continuation of application No. 15/333,420, filed on Oct. 25, 2016, now Pat. No. 9,746,413, which is a
(Continued)

(51) Int. Cl.
*G01N 1/02* (2006.01)
*G01N 1/28* (2006.01)
(Continued)

(52) U.S. Cl.
CPC .... *G01N 15/1484* (2013.01); *B01L 3/502715* (2013.01); *B01L 3/502746* (2013.01);
(Continued)

(58) Field of Classification Search
CPC ..... B01L 2200/0652; B01L 2300/0816; B01L 3/502715; B01L 3/502761;
(Continued)

(56) References Cited

U.S. PATENT DOCUMENTS

| 644,134 A | 2/1900 | Gastineau |
| 4,551,435 A | 11/1985 | Liberti et al. |

(Continued)

FOREIGN PATENT DOCUMENTS

| EP | 2414548 A2 | 2/2012 |
| WO | 035909 | 5/2003 |

(Continued)

OTHER PUBLICATIONS

Guo, P. et al. Microfluidic capture and release of bacteria in a conical nanopore array. Lab Chip. vol. 12, p. 558-561, 2012, published online Nov. 2011.
(Continued)

*Primary Examiner* — Jennifer Wecker
(74) *Attorney, Agent, or Firm* — Jeffrey Schox

(57) ABSTRACT

A cell capture system including an array, an inlet manifold, and an outlet manifold. The array includes a plurality of parallel pores, each pore including a chamber and a pore channel, an inlet channel fluidly connected to the chambers of the pores; an outlet channel fluidly connected to the pore channels of the pores. The inlet manifold is fluidly connected to the inlet channel, and the outlet channel is fluidly connected to the outlet channel. A cell removal tool is also disclosed, wherein the cell removal tool is configured to remove a captured cell from a pore chamber.

20 Claims, 12 Drawing Sheets

Related U.S. Application Data continuation of application No. 14/607,918, filed on Jan. 28, 2015, now Pat. No. 9,513,195, which is a continuation of application No. 13/557,510, filed on Jul. 25, 2012, now Pat. No. 9,103,754.

(60) Provisional application No. 61/513,785, filed on Aug. 1, 2011.

(51) Int. Cl.
| | | |
|---|---|---|
| *G01N 1/20* | (2006.01) | |
| *B01L 3/00* | (2006.01) | |
| *G01N 15/14* | (2006.01) | |
| *G01N 1/40* | (2006.01) | |
| *C12M 1/00* | (2006.01) | |
| *G01N 15/00* | (2006.01) | |
| *G01N 15/10* | (2006.01) | |

(52) U.S. Cl.
CPC ....... *B01L 3/502761* (2013.01); *C12M 47/04* (2013.01); *G01N 1/20* (2013.01); *G01N 1/28* (2013.01); *G01N 1/40* (2013.01); *G01N 1/405* (2013.01); *B01L 2200/0652* (2013.01); *B01L 2200/0668* (2013.01); *B01L 2300/0636* (2013.01); *B01L 2300/0654* (2013.01); *B01L 2300/0672* (2013.01); *B01L 2300/0816* (2013.01); *B01L 2300/0819* (2013.01); *B01L 2300/0848* (2013.01); *B01L 2300/0877* (2013.01); *B01L 2300/168* (2013.01); *B01L 2400/086* (2013.01); *G01N 2015/0065* (2013.01); *G01N 2015/1006* (2013.01)

(58) Field of Classification Search
CPC ....... B01L 2200/027; B01L 2200/0647; B01L 2200/0684; B01L 2300/06; B01L 2300/0832; B01L 2300/0864; B01L 2300/1822; B01L 2300/1827; B01L 2300/185; B01L 2400/0487; B01L 2400/0683; B01L 3/527; B01L 3/5635; B01L 7/00; B01L 2200/0668; B01L 2300/0636; B01L 2300/0654; B01L 2300/0672; B01L 2300/0819; B01L 2300/0848; B01L 2300/0877; B01L 2300/168; B01L 2400/086; B01L 3/502746; B01L 3/021; C12Q 1/6841; C12Q 1/6844; C12Q 1/686; G01N 2333/70585; G01N 2333/70596; G01N 27/44782; G01N 33/48721; G01N 33/574; G01N 33/57492; G01N 35/0098; G01N 15/1484; G01N 1/20; G01N 1/28; G01N 1/40; G01N 1/405; G01N 2015/0065; G01N 2015/1006; G01N 15/1475; G01N 1/4077; G01N 2015/149; G01N 2035/00158; G01N 2035/1039; G01N 35/00029; G01N 35/1011; C12M 47/04; G06K 9/00127; G06K 9/2027; G06K 9/2036; G06K 9/209
See application file for complete search history.

(56) References Cited

U.S. PATENT DOCUMENTS

| | | |
|---|---|---|
| 4,710,635 A | 12/1987 | Chupp |
| 5,266,269 A | 11/1993 | Niiyama et al. |
| 5,491,343 A | 2/1996 | Brooker |
| 5,851,488 A | 12/1998 | Saul et al. |
| 5,883,370 A | 3/1999 | Walker et al. |
| 5,888,370 A | 3/1999 | Becker et al. |
| 5,993,630 A | 11/1999 | Becker et al. |
| 5,993,632 A | 11/1999 | Becker et al. |
| 6,016,712 A | 1/2000 | Warden et al. |
| 6,127,177 A | 10/2000 | Toner et al. |
| 6,133,030 A | 10/2000 | Bhatia et al. |
| 6,150,180 A | 11/2000 | Parce et al. |
| 6,174,683 B1 | 1/2001 | Hahn |
| 6,221,663 B1 | 4/2001 | Bhatia et al. |
| 6,228,624 B1 | 5/2001 | Terstappen |
| 6,281,008 B1 | 8/2001 | Komai et al. |
| 6,287,832 B1 | 9/2001 | Becker et al. |
| 6,365,362 B1 | 4/2002 | Terstappen et al. |
| 6,410,724 B1 | 6/2002 | Dejean et al. |
| 6,433,134 B1 | 8/2002 | Patron et al. |
| 6,525,997 B1 | 2/2003 | Narayanaswami et al. |
| 6,563,634 B2 | 5/2003 | Shimada et al. |
| 6,613,525 B2 | 9/2003 | Nelson et al. |
| 6,623,983 B1 | 9/2003 | Terstappen et al. |
| 6,641,708 B1 | 11/2003 | Becker et al. |
| 6,645,731 B2 | 11/2003 | Terstappen et al. |
| 6,692,952 B1 | 2/2004 | Braff et al. |
| 6,790,330 B2 | 9/2004 | Gascoyne et al. |
| 6,821,484 B1 | 11/2004 | Gregersen |
| 6,861,259 B2 | 3/2005 | Columbus |
| 6,960,449 B2 | 11/2005 | Wang et al. |
| 7,008,789 B2 | 3/2006 | Gambini et al. |
| 7,035,170 B2 | 4/2006 | Narayanaswami et al. |
| 7,046,357 B2 | 5/2006 | Weinberger et al. |
| 7,148,492 B2 | 12/2006 | Loney et al. |
| 7,172,866 B2 | 2/2007 | Hahn et al. |
| 7,198,901 B1 | 4/2007 | Rachlin |
| 7,217,520 B2 | 5/2007 | Tsinberg et al. |
| 7,238,521 B2 | 7/2007 | Hahn et al. |
| 7,248,352 B2 | 7/2007 | Hamamatsu et al. |
| 7,258,990 B2 | 8/2007 | Falcovitz-Gerassi et al. |
| 7,266,777 B2 | 9/2007 | Scott et al. |
| 7,294,468 B2 | 11/2007 | Bell et al. |
| 7,316,897 B2 | 1/2008 | Bisconte de Saint Julien et al. |
| 7,332,288 B2 | 2/2008 | Terstappen et al. |
| 7,338,760 B2 | 3/2008 | Gong et al. |
| 7,354,389 B2 | 4/2008 | Kureshy et al. |
| 7,439,062 B2 | 10/2008 | Bhatt et al. |
| 7,449,558 B2 | 11/2008 | Yao et al. |
| 7,449,778 B2 | 11/2008 | Sander |
| 7,507,528 B2 | 3/2009 | Albert et al. |
| 7,588,672 B2 | 9/2009 | Unger et al. |
| 7,595,157 B2 | 9/2009 | Tsinberg |
| 7,597,528 B2 | 10/2009 | Rodi |
| 7,604,777 B2 | 10/2009 | Columbus |
| 7,638,464 B2 | 12/2009 | Fagnani et al. |
| 7,695,956 B2 | 4/2010 | Tsinberg et al. |
| 7,704,322 B2 | 4/2010 | Hansen et al. |
| 7,710,563 B2 | 5/2010 | Betzig et al. |
| 7,738,320 B2 | 6/2010 | Taha |
| 7,763,704 B2 | 7/2010 | Ding et al. |
| 7,815,863 B2 | 10/2010 | Kagan et al. |
| 7,858,757 B2 | 12/2010 | Hollmann et al. |
| 7,863,012 B2 | 1/2011 | Rao et al. |
| 7,901,950 B2 | 3/2011 | Connelly et al. |
| 7,964,349 B2 | 6/2011 | Bell et al. |
| 8,008,032 B2 | 8/2011 | Forsyth et al. |
| 8,013,298 B2 | 9/2011 | Khursheed |
| 8,021,614 B2 | 9/2011 | Huang et al. |
| 8,103,080 B2 | 1/2012 | George et al. |
| 8,105,769 B2 | 1/2012 | Bell et al. |
| 8,105,780 B2 | 1/2012 | Su et al. |
| 8,131,053 B2 | 3/2012 | Ortyn et al. |
| 8,158,410 B2 | 4/2012 | Tang et al. |
| 8,174,698 B2 | 5/2012 | Peter et al. |
| 8,175,371 B2 | 5/2012 | George et al. |
| 8,186,913 B2 | 5/2012 | Toner et al. |
| 8,232,112 B2 | 7/2012 | Willson et al. |
| 8,293,524 B2 | 10/2012 | Ionescu-Zanetti et al. |
| 8,304,230 B2 | 11/2012 | Toner et al. |
| 8,329,422 B2 | 12/2012 | Rao et al. |
| 8,372,579 B2 | 2/2013 | Toner et al. |
| 8,372,584 B2 | 2/2013 | Shoemaker et al. |
| 8,406,498 B2 | 3/2013 | Ortyn et al. |
| 8,465,916 B2 | 6/2013 | Bell et al. |

(56) References Cited

U.S. PATENT DOCUMENTS

| | | |
|---|---|---|
| 8,628,923 B2 | 1/2014 | Hamilton et al. |
| 8,658,418 B2 | 2/2014 | Daridon |
| 8,680,025 B2 | 3/2014 | Cooney |
| 8,730,479 B2 | 5/2014 | Ness et al. |
| 8,765,454 B2 | 7/2014 | Zhou et al. |
| 8,771,609 B2 | 7/2014 | Ehben et al. |
| 8,802,367 B2 | 8/2014 | Taniguchi et al. |
| 8,936,945 B2 | 1/2015 | Handique et al. |
| 8,986,988 B2 | 3/2015 | Karnik et al. |
| 9,103,754 B2 | 8/2015 | Handique et al. |
| 9,110,026 B2 | 8/2015 | Collins |
| 9,133,499 B2 | 9/2015 | Di Carlo et al. |
| 9,145,540 B1 | 9/2015 | Deutsch et al. |
| 9,174,216 B2 | 11/2015 | Handique et al. |
| 9,188,586 B2 | 11/2015 | Fan et al. |
| 9,194,001 B2 | 11/2015 | Brenner |
| 9,200,245 B2 | 12/2015 | Deutsch et al. |
| 9,201,060 B2 | 12/2015 | Voldman et al. |
| 9,249,459 B2 | 2/2016 | Hamilton et al. |
| 9,260,753 B2 | 2/2016 | Xie et al. |
| 9,290,808 B2 | 3/2016 | Fodor et al. |
| 9,290,809 B2 | 3/2016 | Fodor et al. |
| 9,304,065 B2 | 4/2016 | Fowler et al. |
| 9,315,768 B2 | 4/2016 | Vrouwe et al. |
| 9,315,857 B2 | 4/2016 | Fu et al. |
| 9,329,170 B2 | 5/2016 | Clarke et al. |
| 9,364,829 B2 | 6/2016 | Heid et al. |
| 9,410,201 B2 | 8/2016 | Hindson et al. |
| 9,429,500 B2 | 8/2016 | Fowler et al. |
| 9,506,845 B2 | 11/2016 | Fowler et al. |
| 9,507,609 B2 | 11/2016 | Glazer et al. |
| 9,513,195 B2 | 12/2016 | Handique et al. |
| 9,567,645 B2 | 2/2017 | Fan et al. |
| 9,567,646 B2 | 2/2017 | Fan et al. |
| 9,598,736 B2 | 3/2017 | Fan et al. |
| 9,610,581 B2 | 4/2017 | Handique et al. |
| 9,637,799 B2 | 5/2017 | Fan et al. |
| 9,701,998 B2 | 7/2017 | Hindson et al. |
| 9,707,562 B2 | 7/2017 | Handique et al. |
| 9,708,659 B2 | 7/2017 | Fodor et al. |
| 9,757,707 B2 | 9/2017 | Husain et al. |
| 9,802,193 B2 | 10/2017 | Handique et al. |
| 9,840,732 B2 | 12/2017 | Anderson et al. |
| 9,845,502 B2 | 12/2017 | Fodor et al. |
| 9,850,483 B2 | 12/2017 | Clarke et al. |
| 9,952,126 B2 | 4/2018 | Fowler et al. |
| 9,995,662 B2 | 6/2018 | Husain et al. |
| 2004/0106130 A1 | 6/2004 | Besemer et al. |
| 2004/0229349 A1 | 11/2004 | Daridon |
| 2005/0014201 A1 | 1/2005 | Deuthsch |
| 2006/0128006 A1* | 6/2006 | Gerhardt ............ B01L 3/502761 435/287.1 |
| 2006/0257992 A1 | 11/2006 | McDevitt et al. |
| 2008/0003224 A1 | 1/2008 | Fong et al. |
| 2008/0014589 A1 | 1/2008 | Link et al. |
| 2008/0090239 A1 | 4/2008 | Shoemaker et al. |
| 2008/0206751 A1 | 8/2008 | Squirrell et al. |
| 2009/0061450 A1 | 3/2009 | Hunter |
| 2009/0081773 A1 | 3/2009 | Kaufman |
| 2009/0317836 A1 | 12/2009 | Kuhn et al. |
| 2010/0233693 A1 | 9/2010 | Kopf-Sill et al. |
| 2010/0261179 A1 | 10/2010 | Betley et al. |
| 2010/0304978 A1 | 12/2010 | Deng et al. |
| 2011/0053151 A1 | 3/2011 | Hansen et al. |
| 2011/0117634 A1 | 5/2011 | Halamish et al. |
| 2011/0143964 A1* | 6/2011 | Zhou ..................... B01L 3/5027 506/26 |
| 2011/0227558 A1 | 9/2011 | Mannion et al. |
| 2012/0129190 A1 | 5/2012 | Chiu et al. |
| 2012/0156675 A1 | 6/2012 | Luerssen et al. |
| 2012/0164679 A1 | 6/2012 | Vrouwe et al. |
| 2013/0171628 A1 | 7/2013 | Di et al. |
| 2014/0173443 A1 | 6/2014 | Hawkins, III et al. |
| 2014/0213487 A1 | 7/2014 | Freudenthal et al. |
| 2014/0315237 A1 | 10/2014 | Masujima et al. |
| 2014/0357511 A1 | 12/2014 | Handique et al. |
| 2014/0370612 A1 | 12/2014 | Bassler et al. |
| 2015/0089359 A1 | 3/2015 | Brisebois |
| 2015/0093306 A1 | 4/2015 | Thorne et al. |
| 2015/0133319 A1 | 5/2015 | Fu et al. |
| 2015/0376609 A1 | 12/2015 | Hindson et al. |
| 2016/0024572 A1 | 1/2016 | Shishkin et al. |
| 2016/0024761 A1 | 1/2016 | Korb |
| 2016/0053253 A1 | 2/2016 | Salathia et al. |
| 2016/0060621 A1 | 3/2016 | Agresti et al. |
| 2016/0130649 A1 | 5/2016 | Xie et al. |
| 2016/0209319 A1 | 7/2016 | Adalsteinsson et al. |
| 2016/0251714 A1 | 9/2016 | Conant et al. |
| 2016/0289669 A1 | 10/2016 | Fan et al. |
| 2016/0314242 A1 | 10/2016 | Schnall-Levin et al. |
| 2017/0044525 A1 | 2/2017 | Kaper et al. |
| 2017/0307502 A1 | 10/2017 | Mason et al. |
| 2017/0320038 A1 | 11/2017 | Husain et al. |
| 2017/0321252 A1 | 11/2017 | Hindson et al. |
| 2017/0335385 A1 | 11/2017 | Hindson et al. |
| 2017/0356027 A1 | 12/2017 | Hindson et al. |
| 2018/0030515 A1 | 2/2018 | Regev et al. |
| 2018/0037942 A1 | 2/2018 | Fu |
| 2018/0051321 A1 | 2/2018 | Hindson et al. |
| 2018/0080075 A1 | 3/2018 | Brenner et al. |
| 2018/0094298 A1 | 4/2018 | Hindson et al. |
| 2018/0094312 A1 | 4/2018 | Hindson et al. |
| 2018/0105808 A1 | 4/2018 | Mikkelsen et al. |
| 2018/0112266 A1 | 4/2018 | Hindson et al. |
| 2018/0127744 A1 | 5/2018 | Hu et al. |
| 2018/0127823 A1 | 5/2018 | Shekhar et al. |
| 2018/0274027 A1 | 9/2018 | Hindson et al. |
| 2018/0282804 A1 | 10/2018 | Hindson et al. |

FOREIGN PATENT DOCUMENTS

| | | |
|---|---|---|
| WO | 098696 | 9/2006 |
| WO | 2010120818 A2 | 10/2010 |
| WO | 2018013723 A1 | 1/2018 |
| WO | 2018058073 A2 | 3/2018 |

OTHER PUBLICATIONS

Lindstrom, Sara (Royal Institute of Technology, Stockholm, Sweden, 2009, pp. 1-80).

Sugio et al. (Sensors and Actuators, B99, 2004, pp. 156-162).

Seale, K. T. et al. "Mirrored pyramidal wells for simultaneous multiple vantage point microscopy." Journal of Microscopy (2008) 232 1-6. (Year: 2008).

Tan, Wei-Heang et al. "A trap-and-release integrated microfluidic system for dynamic microarray applications." PNAS (2007)104 1146-1151. (Year: 2007).

* cited by examiner

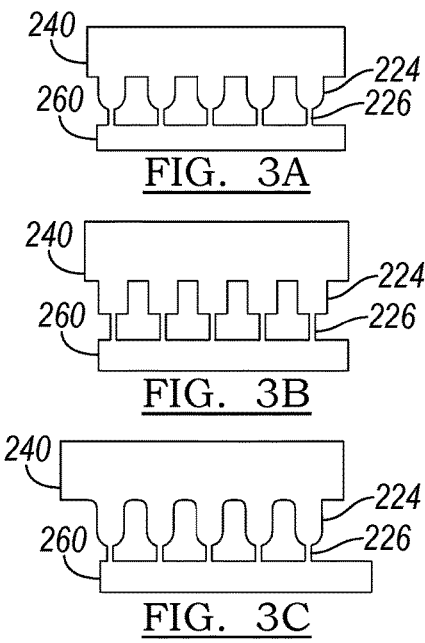
FIG. 3A
FIG. 3B
FIG. 3C
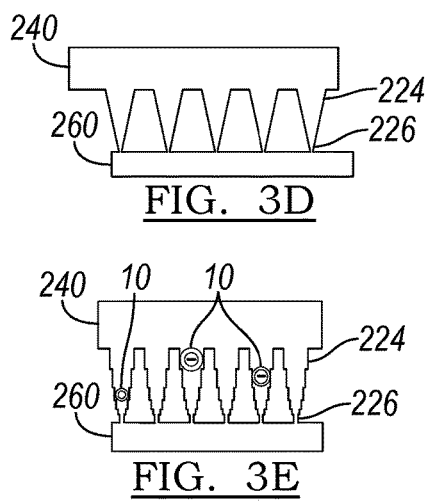
FIG. 3D
FIG. 3E
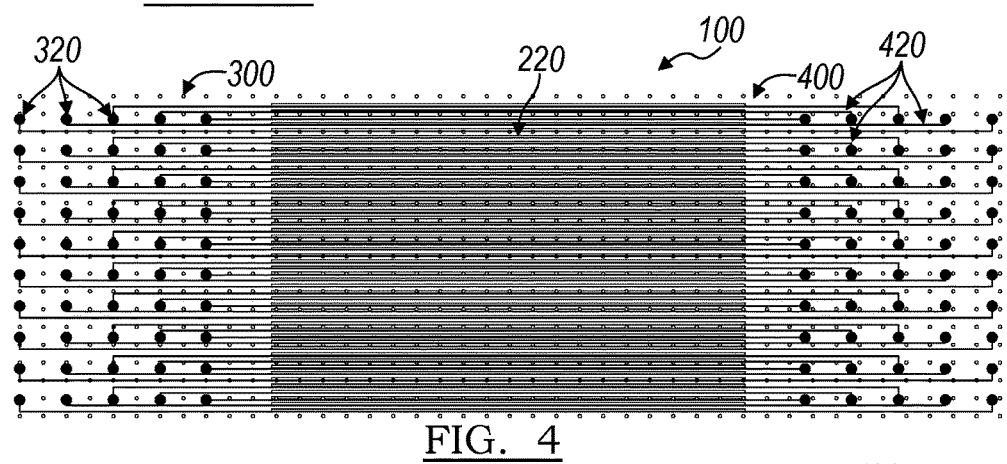
FIG. 4
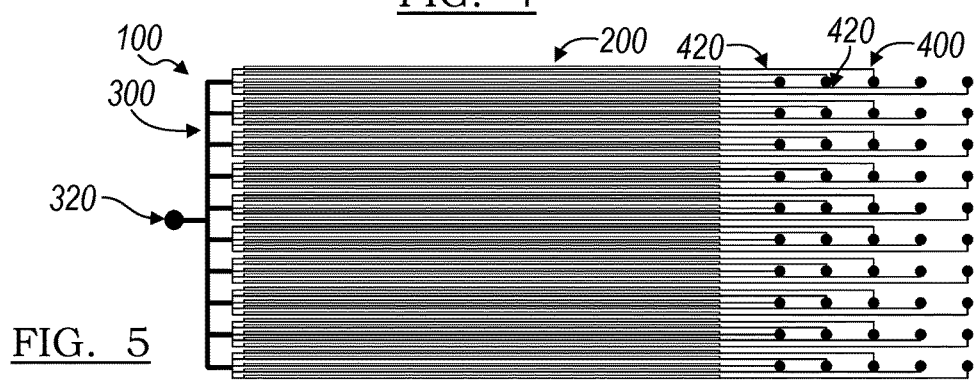
FIG. 5

| STEP # | CROSS SECTION | PROCESS DESCRIPTION |
|---|---|---|
| 1. | 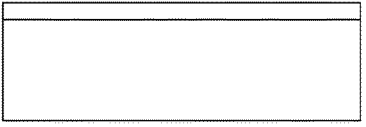 | 1. Oxidation of Silicon Wafer |
| 2. | 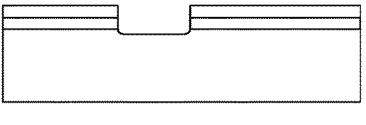 | 1. Photolithography of standard positive resist.<br>2. Etching of Silicon oxide |
| 3. | 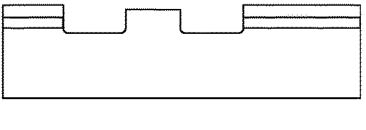 | 1. Remove Photoresist<br>2. Photolithography of standard positive resist. |
| 4. | 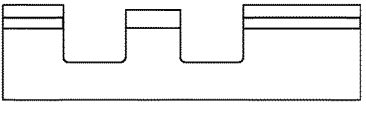 | 1. Silicon Etching (30-40 μm) |
| 5. | 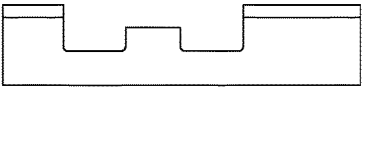 | 1. Remove photoresist<br>2. Silicon Etching (8-10 micron)<br>3. Dicing of individual devices |
| 6. | 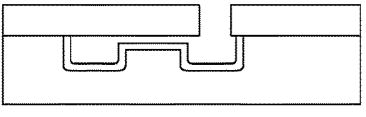 | 1. Anodic bonding of device with glass piece (with pre-drilled holes) |

FIG. 13

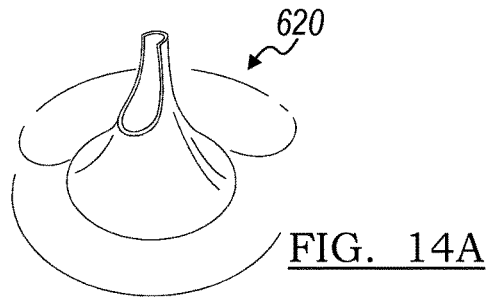 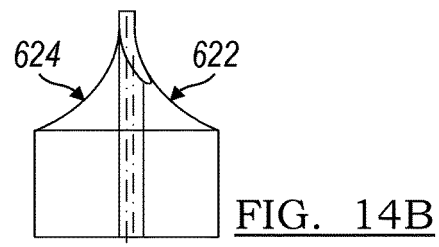
FIG. 14A    FIG. 14B
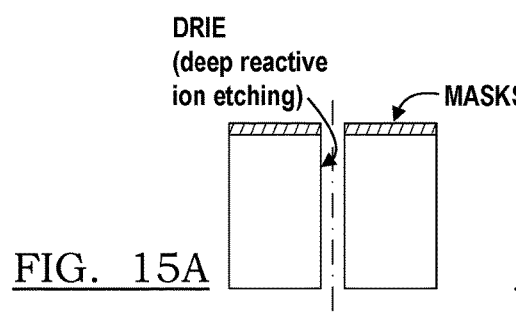 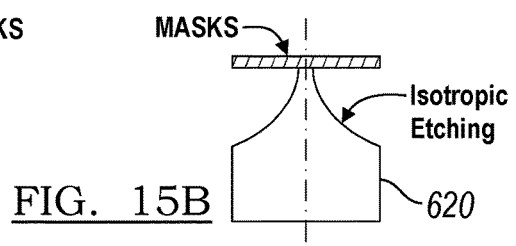
FIG. 15A    FIG. 15B
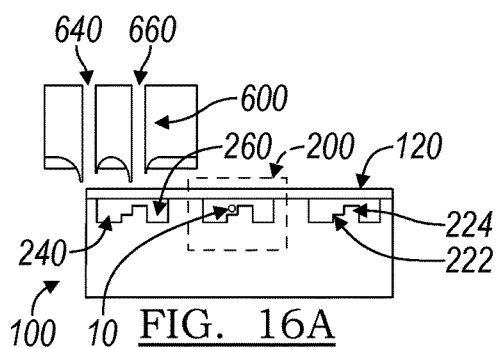 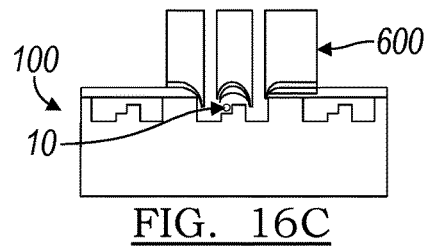
FIG. 16A    FIG. 16C
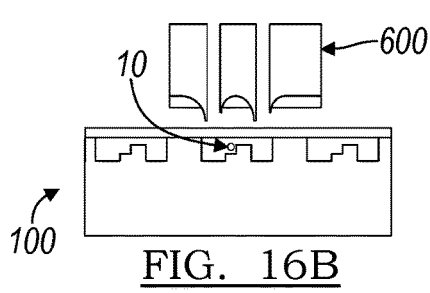 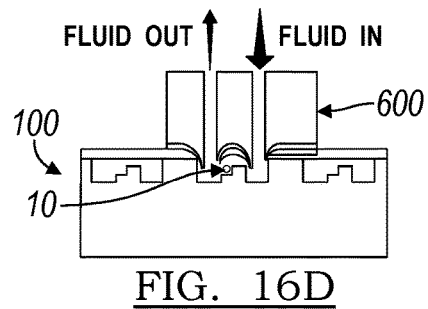
FIG. 16B    FIG. 16D

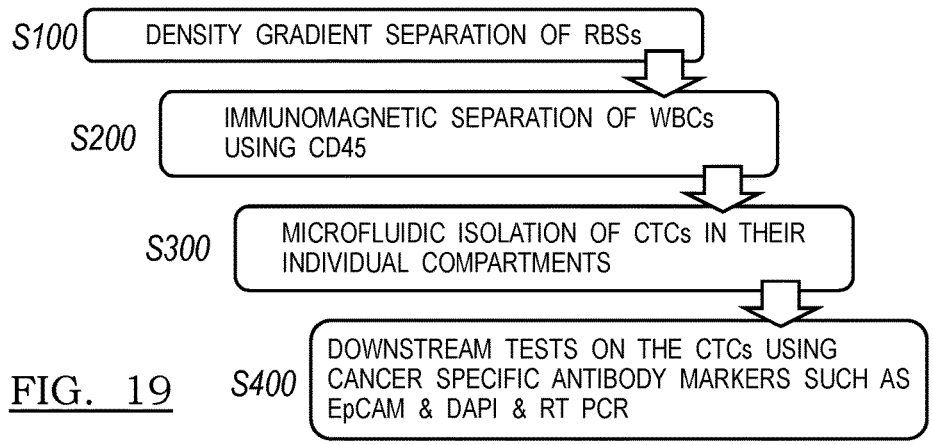
FIG. 19
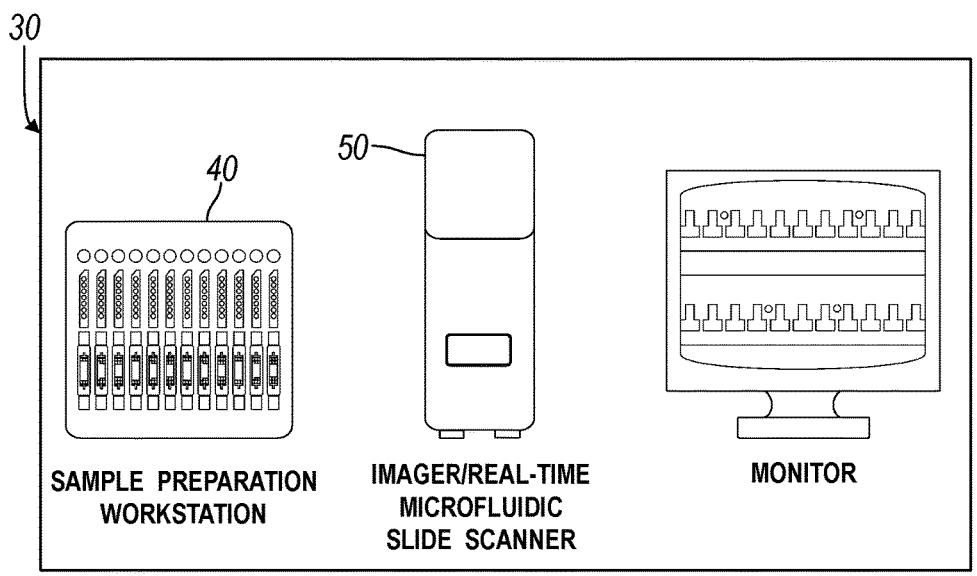
FIG. 20
FIG. 21

CELL CAPTURE SYSTEM AND METHOD OF USE

CROSS-REFERENCE TO RELATED APPLICATIONS

This application is a continuation of U.S. patent application Ser. No. 15/333,420 (now U.S. Pat. No. 9,746,413), filed 25 Oct. 2016, which is a is a continuation of U.S. patent application Ser. No. 14/607,918 (now U.S. Pat. No. 9,513,195), filed 28 Jan. 2015, which is a continuation of U.S. patent application Ser. No. 13/557,510 (now U.S. Pat. No. 9,103,754), filed 25 Jul. 2012, and claims the benefit of U.S. Provisional Application Ser. No. 61/513,785 filed on 1 Aug. 2011, which are all incorporated in their entirety by this reference.

TECHNICAL FIELD

This invention relates generally to the cell sorting field, and more specifically to a new and useful cell sorting and analysis system within the cell sorting field.

BACKGROUND

With an increased interest in cell-specific drug testing, diagnosis, and other assays, systems that allow for individual cell isolation, identification, and retrieval are becoming more desirable within the field of cellular analysis. Furthermore, with the onset of personalized medicine, low-cost, high fidelity cellular sorting systems are becoming highly desirable. However, preexisting cell capture systems suffer from various shortcomings that prevent widespread adoption for cell-specific testing. For example, flow cytometry requires that the cell be simultaneously identified and sorted, and limits cell observation to a single instance. Flow cytometry fails to allow for multiple analyses of the same cell, and does not permit arbitrary cell subpopulation sorting. Conventional microfluidic devices rely on cell-specific antibodies for cell selection, wherein the antibodies that are bound to the microfluidic device substrate selectively bind to cells expressing the desired antigen. Conventional microfluidic devices fail to allow for subsequent cell removal without cell damage, and only capture the cells expressing the specific antigen; non-expressing cells, which could also be desired, are not captured by these systems. Cellular filters can separate sample components based on size without significant cell damage, but suffer from clogging and do not allow for specific cell identification, isolation, and retrieval.

Thus, there is a need in the cell sorting field to create a new and useful cell capture and analysis system.

BRIEF DESCRIPTION OF THE FIGURES

FIGS. 3A, 3B, 3C, 3D, and 3E are schematic representations of a first, second, third, fourth, and fifth pore variation, respectively.

FIG. 4 is a top view of a variation of the cell capture system.

FIG. 5 is a top view of a second variation of the cell capture system.

FIG. 13 is a schematic representation of a second method of cell capture system manufacture.

FIGS. 14A and 14B are a perspective view and a side view of a first variation of the cell removal tool, respectively.

FIGS. 15A and 15B are a schematic representation of a method of manufacture for a first variation of the cell removal tool.

FIGS. 16A, 16B, 16C, and 16D are schematic representations of a first variation of cell removal, including cell of interest identification, cell removal tool alignment, cell removal tool perforation of the top layer, and cell of interest removal, respectively.

FIG. 19 is a variation of cell capture system use, including sample preparation.

FIG. 20 is a schematic representation of an integrated platform with which the cell capture system can be used.

FIG. 21 is a schematic representation of a fluidic manifold.

DESCRIPTION OF THE PREFERRED EMBODIMENTS

The following description of the preferred embodiments of the invention is not intended to limit the invention to these preferred embodiments, but rather to enable any person skilled in the art to make and use this invention.

Figure 1:
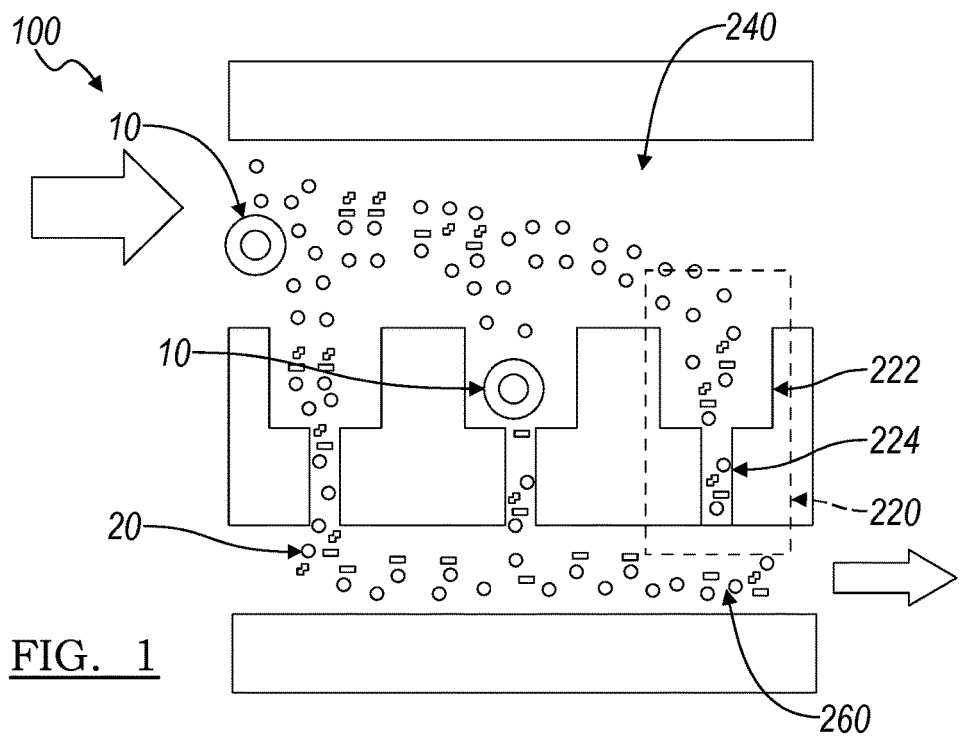
FIG. 1 is a schematic representation of the cell capture system.
Figure 2:
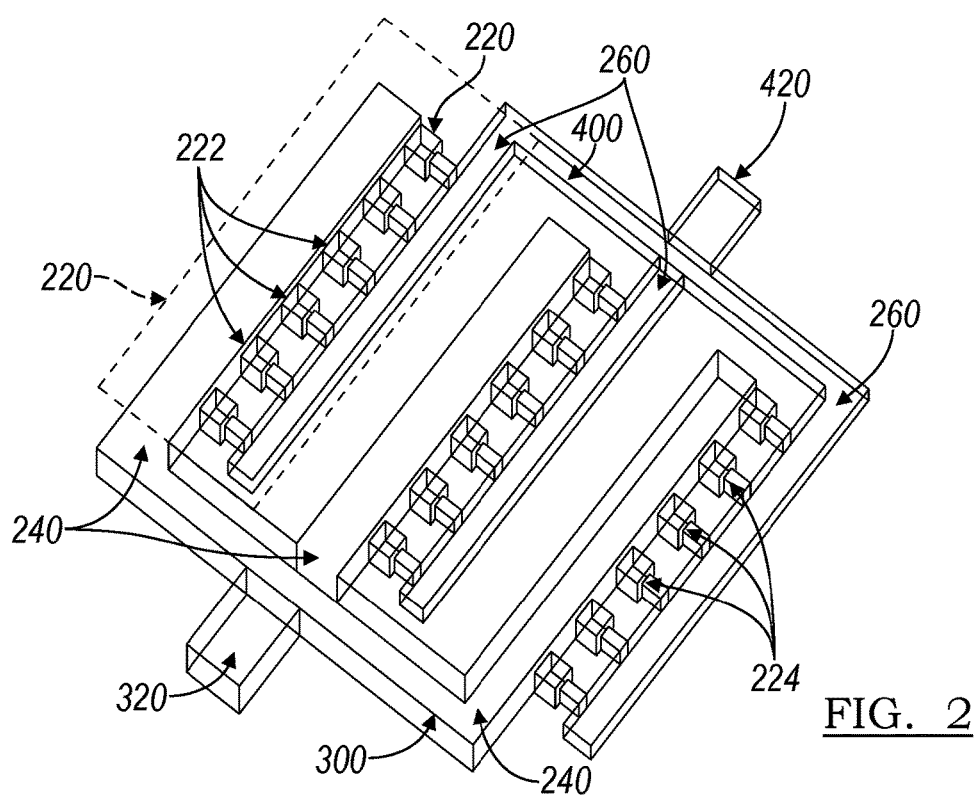
FIG. 2 is a perspective view of a variation of the cell capture system.

As shown in FIGS. 1 and 2, the cell capture system 100 includes an array 200, an inlet manifold 300, and an outlet manifold 400. The array 200 includes a plurality of pores 220, each pore 220 including a chamber 222 fluidly connected to a pore channel 224; an inlet channel 240 fluidly connected to the chamber 222; and an outlet channel 260 fluidly connected to the pore channel 224. The inlet manifold 300 is preferably fluidly coupled to the inlet channel 240, and the outlet manifold 400 is preferably fluidly coupled to the outlet channel 260. The cell capture system 100 functions to isolate, capture, and hold cells, more preferably single cells, at known, addressable locations. Once cells are captured in defined locations determined by single cell capture chambers, the fluidic network can be used to provide and deliver multiple reagents simultaneously or sequentially to enable a variety of cellular, sub-cellular or molecular reactions to be performed in each of the single cells. The cell capture system 100 can also allow optical interrogation and detection of events on each of the captured cells at a single cell level. The cell capture system 100 can additionally function to selectively release or facilitate selective removal of one or more of the captured cells. The cell capture system 100 can confer the benefits of real-time cell tracking, viable cell retrieval, and selective downstream molecular testing, either in the same microfluidic chip or off-chip. The cell capture system 100 can be used to capture circulating tumor cells (CTCs), but can alternatively be used to capture any other suitable cell of possible interest. The cell capture system 100 is preferably defined on a chip, more preferably a microfluidic chip, but can alternatively be located on or defined by any suitable substrate 110.

The cell capture system 100 preferably achieves individual cell capture and retention without antibody coated chambers 222, and preferably maintains the viability of the cells throughout isolation, capture, retention, and removal. The cell capture system 100 preferably additionally minimizes clogging. The cell capture system 100 preferably accomplishes this by utilizing suitably sized pores 220 and by leveraging massively parallel flow, such that the cells near the sample inlet 320 preferably experience substantially the same pressure as the cells distal the sample inlet 320 while minimizing the total pressure differential required to flow liquid at high rates through the cell capture system. The variation in pressure felt by cells at the respective ends of the array is preferably less than 50% or 75% of the inlet pressure, but can alternatively be more or less. The sample flow is preferably substantially laminar, but can alternatively have any other suitable flow characteristics. The sample flow path is preferably substantially unidirectional, but can alternatively be bi-directional. Cell sorting and viability maintenance can additionally be accomplished by controlling the sample flow rate through the system, or through any other suitable means.

In operation, the cell capture system 100 preferably receives a sample under positive pressure through the inlet manifold 300. Sample flow through the cell capture system 100 can be additionally or alternatively encouraged by providing negative pressure at the outlet manifold 400. Alternatively, actuation pressure may be cycled in a pulse-width modulation fashion or sinusoidal fashion to provide net actuation pressure, either net positive at the inlet or net negative at the outlet. The sample preferably flows through the inlet manifold 300 to the inlet channel 240, through the chambers 222 and pore channels 224 to the outlet channel 260, and out of the cell capture system 100 through the outlet manifold 400. Cells of a predetermined size are preferably trapped within the chamber 222 as the sample flows through the pores 220, wherein the pore channel 224 dimensions preferably prevent flow of certain cell sizes therethrough. For example, in the variation of the cell capture system 100 configured to capture CTCs, the chambers 222 are preferably dimensioned larger than a CTC, and the pore channels 224 are preferably dimensioned smaller than the CTC.

As shown in FIGS. 1 and 2, the array 200 of the cell capture system 100 functions to capture cells of interest in addressable, known locations. The array 200 includes a plurality of pores 220, each pore 220 including a chamber 222 fluidly connected to a pore channel 224; an inlet channel 240 fluidly connected to the chamber 222; and an outlet channel 260 fluidly connected to the pore channel 224. The array 200 is preferably substantially linear with a substantially constant width, but can alternatively be nonlinear and/or have a variable width. The array 200 preferably includes a linear inlet channel 240, a linear outlet channel 260 arranged parallel to the inlet channel 240, and a plurality of parallel pores 220 arranged therebetween, normal to the inlet 320 and outlet channels 260. However, the array 200 can alternatively be substantially linear with a diverging or converging width, wherein the linear inlet 320 and outlet channels 260 are arranged at an angle, and consecutive pores 220 have increasing or decreasing lengths. The array 200 can alternatively be serpentine, boustrophedonic, or have any other suitable geometry.

The cell capture system 100 preferably includes one or more arrays 200. More preferably, the cell capture system 100 includes multiple arrays 200 aligned in parallel, such that the outlet channel 260 of a first array 200 is preferably oriented parallel to the inlet channel 240 of an adjacent array 200. The multiple arrays 200 are preferably substantially identical, wherein the pores 220 of the multiple arrays 200 preferably have the same or similar chamber 222 dimensions and pore channel 224 dimensions, the inlet channels 240 preferably have similar lengths and widths, and the outlet channels 260 preferably have similar lengths and widths. However, different arrays 200 within the cell capture system 100 can have different pore 220 characteristics, different inlet channel 240 characteristics, and/or different outlet channel 260 characteristics. For example, a cell capture system 100 can include multiple arrays 200, wherein a first array 200 has pores 220 with a large pore channel 224 width that captures large cells, a second array 200 has pores 220 with a medium pore channel 224 width that captures medium sized cells, and a third array 200 has pores 220 with a small pore channel 224 width that captures small cells.

Figure 8:
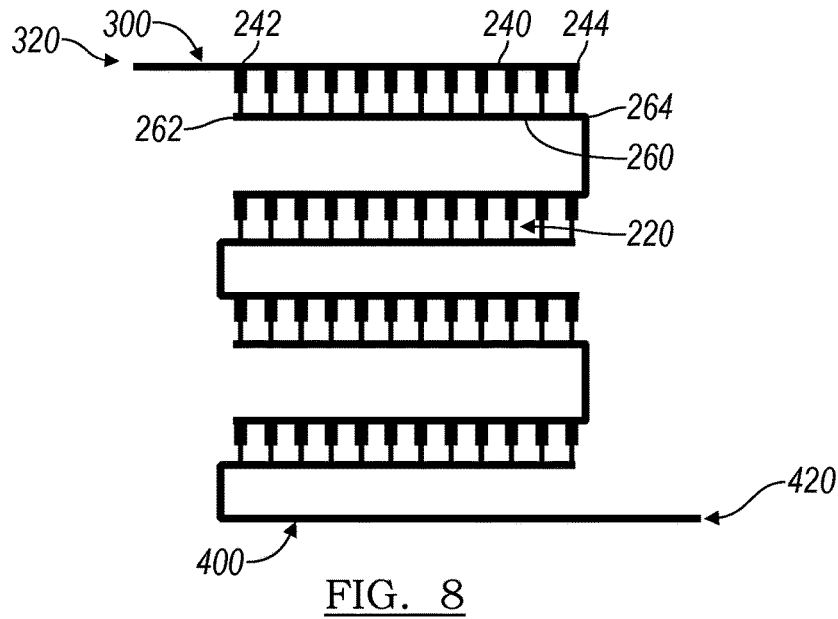
FIG. 8 is a top view of a fifth variation of the cell capture system.

The multiple arrays 200 are preferably fluidly coupled in parallel by the inlet manifold 300. Alternatively, the multiple arrays 200 can be fluidly coupled in series, as shown in FIG. 8, wherein the outlet channel 260 of an upstream array 200 feeds into the inlet channel 240 of an adjacent downstream array 200.

The pores 220 of the array 200 function to capture and retain cells. More preferably, the pores 220 of the array 200 capture and retain a single cell. The pores 220 preferably include a chamber 222 configured to hold a cell, and a pore channel 224 fluidly connected to the chamber 222. The chamber 222 preferably has a length that prevents cell egress due to crossflow within the inlet channel 240, and a width or a depth that prevents excessive cell movement but allows for the cell to move enough such that the cell does not block the pore channel junction. The end of the pore channel 224 proximal the chamber 222 preferably has a width that prevents the cell of interest 10 from passing through, while permitting smaller sample component (e.g. lysed cells, cellular components, etc.) flow therethrough. The end of the pore channel 224 proximal the chamber 222 is preferably smaller than the diameter of the cell of interest 10, but can have any other suitable dimension.

Each array 200 preferably includes multiple pores 220. For example, an array 200 can include 100, 1000, 10,000, 1,000,000, or any suitable number of pores 220. The pores 220 are preferably fluidly coupled in parallel within the array 200, but can alternatively be fluidly coupled in series within the array 200. The pores 220 are preferably arranged in parallel within the array 200, wherein the longitudinal axes of adjacent pores 220 are preferably parallel. However, the pores 220 can be arranged at an angle to adjacent pores 220 within the array 200. The pores 220 of a given array 200 are preferably substantially similar or identical, with chambers 222 of substantially the same dimension and pore channels 224 of substantially the same dimension. However, a single array 200 can have pores 220 with substantially different chamber 222 and pore channel 224 dimensions, with varying chamber 222 lengths, chamber 222 widths, chamber 222 depths, pore channel 224 lengths, pore channel 224 widths, pore channel 224 depths, number of pore channels 224 per pore 220, number of chambers 222 per pore 220, or pores 220 that vary along any other suitable parameter. For example, an array 200 can have multiple pores 220 arranged in parallel, wherein consecutive pores 220 have decreasing pore channel widths.

The chamber 222 of the pore 220 functions to retain a cell. The chamber 222 is preferably fluidly connected to the inlet channel 240 and the pore channel 224. The chamber 222 preferably has a length and width configured to retain an isolated cell, wherein the chamber 222 is dimensioned to prevent cell egress from the chamber 222 due to inlet channel cross-flow. In one variation, this is achieved by controlling the width to height ratio of chamber 222. The width to height ratio of the chamber 222 is preferably 1, but can alternatively be 1.25, 0.5, or any other suitable ratio. The chamber 222 is preferably configured to retain a single cell and to prevent multiple cell retention. In one variation, the chamber 222 is dimensioned such that the height/width of the chamber 222 prevents a second cell from settling to the end of the chamber 222 proximal the pore channel 224 (e.g. the bottom of the chamber 222), and the length of the chamber 222 prevents a single cell egress from the chamber 222 (e.g. the length is longer than the cell diameter), but encourages egress of a second cell from the chamber 222 (e.g. the length is longer than the cell diameter, but shorter than two cell diameters). However, the chamber 222 can be configured to retain multiple cells. The chamber 222 preferably has a length, width and depth between 5-200 microns, but can alternatively have any suitable dimensions. In one variation, the chamber has a length of 50 micrometers, a width of 50 micrometers, and a height of 50 micrometers. In another variation, the chamber has a length of 25 micrometers, a width of 25 micrometers, and a height of 30 micrometers. The chamber 222 preferably has a substantially constant cross-section, but can alternatively have a tapering cross-section, preferably tapering from the inlet channel 240 to the pore channel 224. The variable cross-section can be the cross-section parallel to the broad face of the substrate 112 and/or the cross-section perpendicular to the longitudinal axis of the chamber 222. In one variation, as shown in FIG. 3B, the chamber 222 has a rectangular cross-section, wherein the pore channel 224 connects to a side of the chamber 222 opposing that connected to the inlet channel 240. In another variation, the chamber 222 has a parabolic cross section, as shown in FIG. 3A and FIG. 3C, wherein the pore channel 224 connects to the apex of the parabolic profile. In another variation, as shown in FIG. 3D, the chamber cross section linearly decreases from the inlet channel 240 to the pore channel 224. In another variation, as shown in FIG. 3E, the chamber cross-section decreases stepwise from the inlet channel 240 to the pore channel 224. In this variation, the chamber 222 defines multiple sub-chambers, wherein the multiple sub-chambers are preferably fluidly connected in series, wherein a first sub-chamber is fluidly connected to the inlet channel 240 and the last sub-chamber is fluidly connected to the pore channel 224. The first sub-chamber preferably has the largest width and/or depth, and the last sub-chamber preferably has the smallest width and/or depth. The transition between the inlet channel 240 and the chamber 222 preferably exhibits a convex angle (e.g. a 90° angle), but can alternatively be curved as shown in FIG. 3C. The transition between the chamber 222 and the pore channel 224 preferably also exhibits a convex angle (e.g. a 90° angle), but can alternatively be curved.

The pore channel 224 of the pore 220 functions to filter out the cell of interest 10 and to allow smaller sample components to flow through. The pore channel 224 is preferably fluidly connected to the chamber 222 and the outlet channel 260. More preferably, the pore channel 224 is fluidly connected to the portion of the chamber 222 distal from the inlet channel 240. The pore channel 224 is preferably substantially straight and linear, but can alternatively be curved. The pore channel 224 preferably has a width smaller than the diameter of the cell of interest 10, such that the pore channel 224 prevents cell passage therethrough. The pore channel 224 preferably has a width and depth between 1-25 microns and a length between 5-500 microns, but can have any other suitable width, depth, and length. In one variation, the pore channel 224 has a width of 7-10 micrometers, a depth of 7-10 micrometers, and a length of 5-50 micrometers. The pore channel 224 preferably has a substantially constant cross-section, but can alternatively have a tapering or variable cross section. The pore channel 224 is preferably aligned with its longitudinal axis parallel the longitudinal axis of the chamber 222. More preferably, the pore channel 224 is coaxial with the chamber 222. However, the pore channel 224 can be aligned at an angle with the chamber 222. Each pore 220 preferably includes a single pore channel 224, but can alternatively include multiple pore channels 224, wherein the multiple pore channels 224 preferably extend in parallel from the end of the respective chamber 222 proximal the outlet channel 260.

The inlet channel 240 of the array 200 functions to receive a volume of the sample and to distribute the sample to the pores 220. The inlet channel 240 preferably fluidly connects the inlet manifold 300 to the chambers 222 of the array 200. The inlet channel 240 preferably includes a first end, a second end, and a channel connecting the first and second ends. The inlet channel 240 is preferably fluidly connected to the inlet manifold 300 at the first end, is fluidly connected to the chambers 222 of the array 200 along the inlet channel 240 length, and is preferably fluidly sealed at the second end. The second end can be sealed by the substrate 110 or can be sealed by a sealant, such as a self-sealing laminate (e.g. made of rubber, polyethylene, etc.). However, the inlet channel 240 can include a first and/or second valve disposed within the first and/or second end, wherein the valves can operate between an open and a closed state. The body of the inlet channel 240 is preferably defined by the substrate 110, but can alternatively be partially defined by the substrate 110, wherein the other portions can be defined by self-sealing laminate or any other suitable sealant. The inlet channel 240 is preferably arranged such that the inlet channel longitudinal axis is perpendicular to the longitudinal axes of the chambers 222, but can alternatively be arranged at an angle. The chambers 222 preferably extend from a single side of the inlet channel 240, but can alternatively extend from multiple sides (e.g. opposing sides). The inlet channel 240 is preferably substantially straight, but can alternatively be curved or bent. The inlet channel 240 preferably has a substantially constant cross-section, but can alternatively have a variable cross section. The cross-section can be the cross-section parallel to the inlet channel longitudinal axis or perpendicular to the inlet channel longitudinal axis. In one variation, the inlet channel 240 tapers with distance away from the inlet manifold 300. The inlet channel 240 preferably has a depth and width larger than the diameter of the cell of interest 10. The inlet channel 240 preferably a depth and/or width between 5-200 microns, but can alternatively have any suitable depth and/or width. In one variation, the inlet channel has a width of 50-100 micrometers, and a depth of 50-100 micrometers. The inlet channel 240 preferably has a length that can accommodate all the pores 220 of the array 200. In one variation, the inlet channel 240 preferably has a length longer than the combined widths of the chambers 222. In another variation, the inlet channel 240 extends to the edge of the substrate 110. Each array 200 preferably includes one inlet channel 240, but can alternatively include multiple inlet channels 240. For example, an array 200 can include two inlet channels 240 that feed two sets of pores 220 extending from either side of a central outlet channel 260, wherein each inlet channel 240 feeds one set of pores 220. However, the array 200 can include any suitable configuration of inlet channels 240.

The outlet channel 260 of the array 200 functions to receive a volume of the sample and to distribute the sample to the pores 220. The outlet channel 260 preferably includes a first end, a second end, and a channel connecting the first and second ends. The outlet channel 260 is preferably fluidly connected to the outlet manifold 400 at the second end, fluidly connected to the chambers 222 of the array 200 along the outlet channel 260 length, and is preferably fluidly sealed at the first end. The first end of the outlet channel 260 can be sealed by the substrate 110 or can be sealed by a sealant, such as a self-sealing laminate (e.g. made of rubber, polyethylene, etc.). Alternatively, the outlet channel 260 can include a first and/or second valve disposed within the first and/or second end, wherein the valves can operate between an open and a closed state. The body of the outlet channel 260 is preferably defined by the substrate 110, but can alternatively be partially defined by the substrate 110, wherein the other portions can be defined by self-sealing laminate or any other suitable sealant. The outlet channel 260 is preferably arranged such that the outlet channel longitudinal axis is perpendicular to the longitudinal axes of the chambers 222, but can alternatively be arranged at an angle. The chambers 222 preferably extend from a single side of the outlet channel 260, but can alternatively extend from multiple sides (e.g. opposing sides). The outlet channel 260 is preferably substantially straight, but can alternatively be curved or bent. The outlet channel 260 preferably has a substantially constant cross-section, but can alternatively have a variable cross section. The outlet channel 260 cross-section can be the cross-section parallel outlet channel longitudinal axis or perpendicular the outlet channel longitudinal axis. In one variation, the outlet channel 260 tapers with distance away from the outlet manifold 400. The outlet channel 260 preferably has a depth and width similar to that of the inlet channel 240, but can alternatively have a depth and width smaller or larger than that of the inlet channel 240. The outlet channel 260 preferably a depth and/or width between 5-200 microns, but can alternatively have any suitable depth and/or width. In one variation, the outlet channel has a width of 50-100 micrometers, and a depth of 50-100 micrometers. The outlet channel 260 preferably has a length that can accommodate all the pores 220 of the array 200. In one variation, the outlet channel 260 preferably has a length longer than the combined widths of the chambers 222. In another variation, the outlet channel 260 extends to the edge of the substrate 110. Each array 200 preferably includes one outlet channel 260, but can alternatively include multiple outlet channels 260. For example, an array 200 can include two outlet channels 260 that egress two sets of pores 220 extending from either side of a central inlet channel 240, wherein each outlet channel 260 egresses one set of pores 220.

The inlet manifold 300 of the cell capture system 100 functions to receive a sample and to distribute the sample to the arrays 200. More preferably, the inlet manifold 300 distributes the sample to an inlet channel 240 of an array 200. The inlet manifold 300 preferably additionally includes an inlet 320, wherein the inlet manifold 300 receives the sample from the inlet 320. The inlet manifold 300 preferably provides a substantially linear flow path from the inlet 320 to the inlet channels 240 while substantially minimizing the differences in pressure experienced by different arrays 200 within the system. The inlet manifold 300 is preferably defined within the same substrate broad face as the array 200, but can alternatively be defined through a portion or the entirety of the substrate thickness. The entirety of the inlet manifold 300, except for the inlet 320, is preferably fluidly sealed by the top layer 120.

In one variation, as shown in FIG. 4, the cell capture system 100 includes multiple inlet manifolds 300, one for each inlet channel 240. In this variation, the multiple inlet manifolds 300 can receive a single sample or multiple samples.

Figure 6:
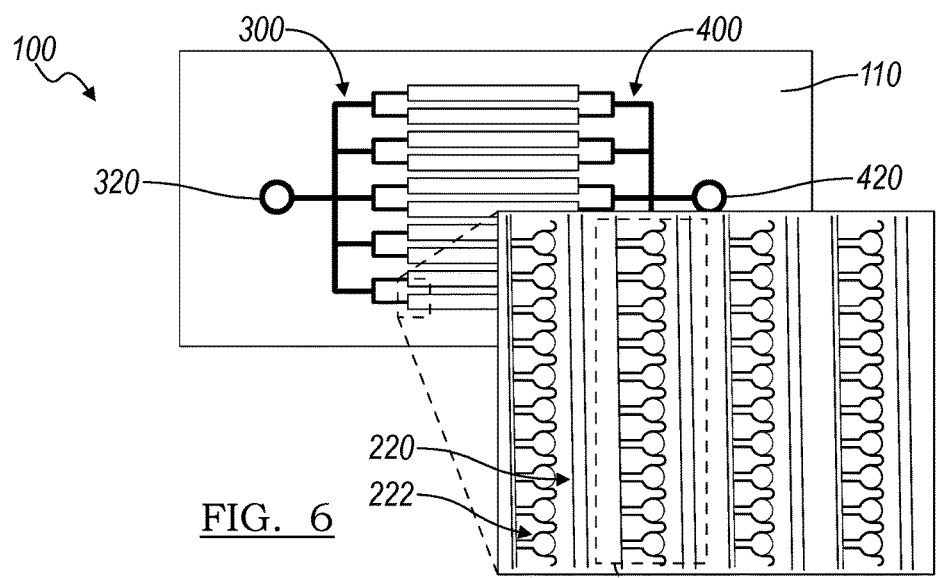
FIG. 6 is a top view of a third variation of the cell capture system.
Figure 7:
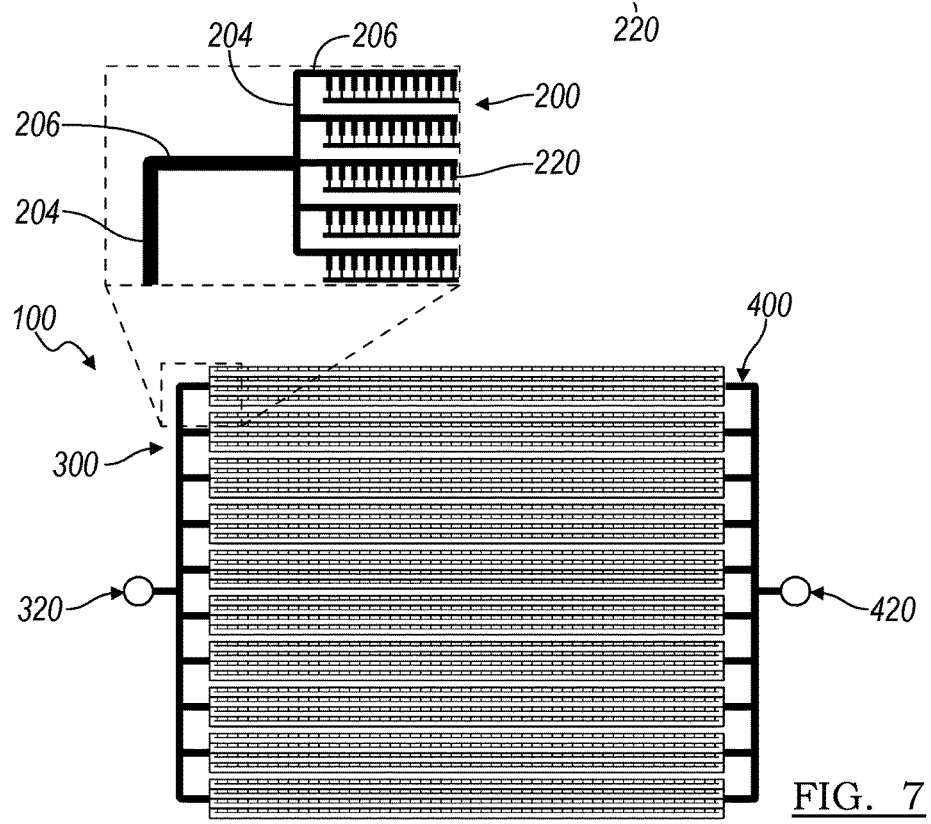
FIG. 7 is a top view of a fourth variation of the cell capture system.

In another variation, as shown in FIGS. 5, 6, and 7, the system includes a single inlet manifold 300 that feeds all the inlet channels 240. The inlet manifold 300 preferably fluidly connects the arrays 200 in parallel to facilitate parallel flow throughout the cell capture system 100. However, the inlet manifold 300 can alternatively fluidly connect the arrays 200 in series or in any suitable combination of series and parallel flow. The inlet manifold 300 preferably includes one or more tiers of inlet sub-manifolds 302. Each inlet sub-manifold 302 preferably includes a main channel 204 and a plurality of feeder channels 206, wherein the feeder channels 206 facilitate sample flow into subsequent sub-manifolds or the inlet channels 240 of the arrays 200. The feeder channels 206 directly fluidly connected to the inlet channels 240 are preferably aligned and coextensive with the inlet channels 240, but can alternatively be perpendicular to the inlet channels 240 or arranged in any suitable configuration. The main channel 204 preferably fluidly connects the feeder channels 206 in parallel. The feeder channels 206 are preferably arranged parallel to the other feeder channels 206, and preferably all extend perpendicularly from one side of the main channel 204. However, the feeder channels 206 can be arranged at an acute angle relative to the main channel 204, extend from opposing sides of the main channel 204, or be otherwise suitably arranged. The sub-manifolds directly fluidly connected to the inlet channels 240 are preferably each coupled to a subset of the arrays 200 to minimize the pressure difference between the arrays 200 proximal the sub-manifold inlet and the arrays 200 distal the sub-manifold inlet 320. However, a single sub-manifold can directly feed all the arrays 200 of the cell capture system 100.

In one variation, the cell capture system 100 includes an inlet manifold 300 with one inlet sub-manifold tier, wherein the inlet sub-manifold 302 includes multiple feeder channels 206, each feeder channel independently fluidly connected to a inlet channel 240 of an array 200.

In another variation, the cell capture system 100 includes an inlet manifold 300 including two tiers of inlet sub-manifolds 302 (as shown in FIG. 5), wherein the feeder channels 206 of the first tier are fluidly connected to the main channels 204 of the second tier, and the feeder channels 206 of the second tier are fluidly connected to the inlet channels 240. The first tier preferably includes one inlet sub-manifold 302, with one main channel 204 and multiple feeder channels 206. The second tier preferably includes multiple inlet sub-manifolds 302, wherein each second tier inlet sub-manifold 302 is fluidly connected to a first tier feeder channel and a subset of the arrays 200 of the cell capture system 100. For example, a second tier inlet sub-manifold 302 can be fluidly connected to four inlet channels 240 of a forty-array 200 cell capture system 100, wherein the second tier inlet sub-manifold 302 includes one main channel 204 and four feeder channels 206, each feeder channel independently fluidly connected to an inlet channel 240. In this variation, the first tier main channel 204 preferably has a larger width and/or height than the second tier main channels 204, and the first tier feeder channels 206 preferably have a larger width and/or height than the second tier feeder channels 206. The second tier feeder channels 206 are preferably substantially the same width and/or height as the inlet channels 240, but can alternatively have different dimensions than the inlet channels 240. In another variation, the inlet manifold 300 includes three tiers of branching inlet sub-manifolds 302. However, the inlet manifold 300 can include any suitable number of inlet sub-manifold tiers.

The inlet 320 of the inlet manifold 300 functions to provide a fluid connection between the cell capture system 100 exterior and interior. More preferably, the inlet 320 provides a fluid connection between the cell capture system 100 exterior and the inlet manifold 300. The cell capture system 100 preferably includes one inlet 320, but can alternatively include multiple inlets 320. Each inlet 320 is preferably fluidly connected to one inlet manifold 300 through a fluid connection (e.g. a channel), but can alternatively be connected to multiple inlet manifolds 300. Each inlet manifold 300 is preferably fluidly connected to one inlet 320, but can alternatively be connected to multiple inlets 320. The longitudinal axis of the inlet 320 is preferably normal to the longitudinal axis of the main channel 204 of the inlet manifold 300, but can alternatively be parallel. The longitudinal axis of the inlet 320 is preferably normal to the broad face of the substrate 112, but can alternatively be parallel to the broad face of the substrate 112, at an angle to the broad face of the substrate 112, or arranged in any suitable manner. In one variation of the cell capture system 100, the inlet 320 is a hole or aperture through a portion of the substrate thickness, extending from a broad face of the substrate 112 to the plane defining the inlet manifold 300. The broad face of the substrate 112 from which the inlet 320 extends can either be the broad face on which the inlet manifold 300 is defined, wherein a fluid connection connecting the inlet 320 and the inlet manifold 300 is also defined on the same broad face, or can be the broad face opposite that on which the inlet manifold is defined 114, wherein the inlet 320 extends through substantially the whole of the substrate thickness to connect with the inlet manifold 300. In another variation of the cell capture system 100, the inlet 320 is a hole or aperture through a side of the substrate 110, wherein the inlet 320 extends in parallel with a broad face of the substrate 112 towards the inlet manifold 300. In this variation, a fluid connection normal to the broad face of the substrate 112 preferably connects the inlet 320 with the inlet manifold 300. However, any suitable configuration of the inlet 320 can be used.

The outlet manifold 400 of the cell capture system 100 functions to receive filtered sample and to egress the filtered sample from the cell capture system 100. More preferably, the outlet manifold 400 receives the filtered sample from an outlet channel 260 of an array 200. The outlet manifold 400 preferably additionally includes an outlet 420, wherein the outlet manifold 400 egresses the filtered sample from the outlet 420. The outlet manifold 400 preferably provides a substantially linear flow path from the outlet channels 260 to the outlet 420, but can alternatively provide a tortuous flow path. The outlet manifold 400 is preferably defined within the same substrate broad face as the array 200, but can alternatively be defined through a portion or the entirety of the substrate thickness, on the opposing broad face of the substrate 112, or on any suitable portion of the substrate 110. The entirety of the outlet manifold 400, except for the outlet 420, is preferably fluidly sealed by the top layer 120.

In one variation, as shown in FIG. 4, the cell capture system 100 includes multiple outlet manifolds 400, one for each outlet channel 260. In this variation, the multiple outlet manifolds 400 can receive a single filtered sample or multiple filtered samples.

In another variation, as shown in FIGS. 5, 6, and 7, the system includes a single outlet manifold 400 that receives the filtered sample from all the outlet channels 260. The outlet manifold 400 preferably fluidly connects the arrays 200 in parallel, but can alternatively fluidly connect the arrays 200 in series or in any suitable combination of series and parallel flow. The outlet manifold 400 preferably includes one or more tiers of outlet sub-manifolds 402. Each outlet sub-manifold 402 preferably includes a main channel 204 and a plurality of feeder channels 206, wherein the feeder channels 206 facilitate filtered sample flow from upstream sub-manifolds or the outlet channels 260 of the arrays 200 to the main channel 204. The feeder channels 206 directly fluidly connected to the outlet channels 260 are preferably parallel and coextensive with the outlet channels 260, but can alternatively be perpendicular to the outlet channels 260 or arranged in any suitable configuration. The main channel 204 preferably fluidly connects the feeder channels 206 in parallel. The feeder channels 206 are preferably arranged parallel to the other feeder channels 206, and preferably all extend perpendicularly from one side of the main channel 204. However, the feeder channels 206 can arranged at an acute angle relative to the main channel 204, extend from opposing sides of the main channel 204, or be otherwise suitably arranged. The outlet sub-manifolds 402 directly fluidly connected to the outlet channels 260 are preferably each coupled to a subset of the arrays 200. However, a single outlet sub-manifold 402 can directly receive the filtered sample from all the arrays 200 of the cell capture system 100.

In one variation, the cell capture system 100 includes an outlet manifold 400 with one outlet sub-manifold tier, wherein the outlet sub-manifold 402 includes multiple feeder channels 206, each feeder channel independently fluidly connected to a outlet channel 260 of an array 200.

In another variation, the cell capture system 100 includes an outlet manifold 400 including two tiers of outlet sub-manifolds 402, wherein the feeder channels 206 of the first tier are fluidly connected to the main channels 204 of the second tier, and the feeder channels 206 of the second tier are fluidly connected to the outlet channels 260. The first tier preferably includes one outlet sub-manifold 402, with one main channel 204 and multiple feeder channels 206. The second tier preferably includes multiple outlet sub-manifolds 402, wherein each second tier outlet sub-manifold 402 is fluidly connected to a first tier feeder channel and a subset of the arrays 200 of the cell capture system 100. For example, a second tier outlet sub-manifold 402 can be fluidly connected to four outlet channels 260 of a forty-array 200 cell capture system 100, wherein the second tier outlet sub-manifold 402 includes one main channel 204 and four feeder channels 206, each feeder channel independently fluidly connected to an outlet channel 260. In this variation, the first tier main channel 204 preferably has a larger width and/or height than the second tier main channels 204, and the first tier feeder channels 206 preferably have a larger width and/or height than the second tier feeder channels 206. The second tier feeder channels 206 are preferably substantially the same width and/or height as the outlet channels 260, but can alternatively have different dimensions than the outlet channels 260. In another variation, the outlet manifold 400 includes three tiers of branching outlet sub-manifolds 402. In another variation, the outlet manifold 400 includes the same number of tiers as the inlet manifold 300. However, the outlet manifold 400 can include any suitable number of outlet sub-manifold tiers.

The outlet 420 of the outlet manifold 400 functions to provide a fluid connection between the cell capture system 100 interior and the cell capture system 100 exterior. More preferably, the outlet 420 provides a fluid connection between the cell capture system 100 exterior and the outlet manifold 400. The cell capture system 100 preferably includes one outlet 420, but can alternatively include multiple outlets 420. Each outlet 420 is preferably fluidly connected to one outlet manifold 400 through a fluid connection (e.g. a channel), but can alternatively be connected to multiple outlet manifolds 400. Each outlet manifold 400 is preferably fluidly connected to one outlet 420, but can alternatively be connected to multiple outlets 420. The longitudinal axis of the outlet 420 is preferably normal to the longitudinal axis of the main channel 204 of the outlet manifold 400, but can alternatively be parallel. The longitudinal axis of the outlet 420 is preferably normal to the broad face of the substrate 112, but can alternatively be parallel to the broad face of the substrate 112, at an angle to the broad face of the substrate 112, or arranged in any suitable manner. In one variation of the cell capture system 100, the outlet 420 is a hole or aperture through a portion of the substrate thickness, extending from a broad face of the substrate 112 to the plane defining the outlet manifold 400. The broad face of the substrate 112 from which the outlet 420 extends can either be the broad face on which the outlet manifold 400 is defined, wherein a fluid connection connecting the outlet 420 and the outlet manifold 400 is also defined on the same broad face, or the broad face opposite that on which the outlet manifold is defined 114, wherein the outlet 420 extends through substantially the whole of the substrate thickness to connect with the outlet manifold 400. When the inlet 320 is defined on a broad face of the substrate 112, the outlet 420 is preferably defined on the same broad face as the inlet 320, but can alternatively be defined on the opposing broad face. In another variation of the cell capture system 100, the outlet 420 is a hole or aperture through a side of the substrate 110, wherein the outlet 420 extends in parallel with a broad face of the substrate 112 towards the outlet manifold 400. In this variation, a fluid connection normal to the broad face of the substrate 112 preferably connects the outlet 420 with the outlet manifold 400. When the inlet 320 is also defined on a side of the substrate 110, the outlet 420 is preferably defined on a side of the substrate opposing the side defining the inlet 320. However, the outlet 420 can alternatively be defined on the same side or an adjacent side. However, any suitable configuration of the outlet 420 can be used.

Figure 9:
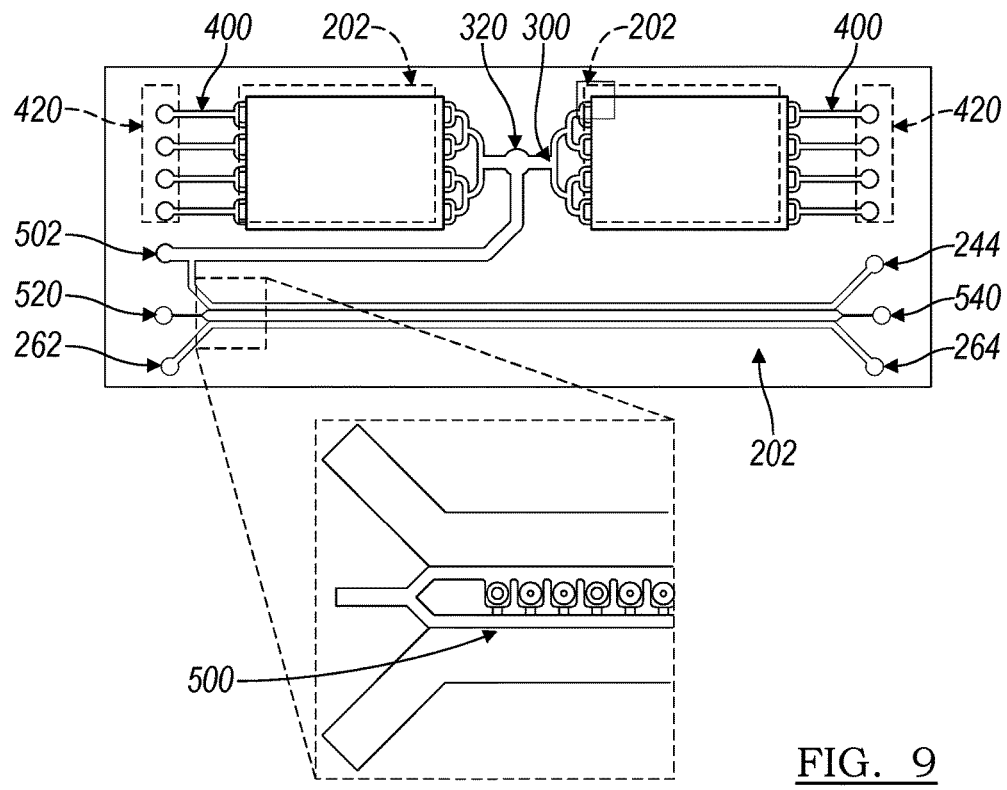
FIG. 9 is a top view of a variation of the cell capture system including an isolation mechanism.

The cell capture system 100 can additionally include an isolation mechanism 500 that functions to isolate cells within individual pores 220. In one variation, the isolation mechanism 500 includes an isolation inlet 520 and an isolation outlet 540, fluidly connected to an array 200, that functions to permit isolation material ingress and egress, respectively. Both the isolation inlet 520 and the isolation outlet 540 are preferably fluidly connected to both the inlet channel 240 and the outlet channel 260. In one variation, as shown in FIG. 9, the isolation inlet 520 can be arranged between the first end of the inlet channel 240 and the outlet channel 260 on the inlet end of the array 200, and the isolation outlet 540 is arranged between the second end of the inlet channel 240 and outlet channel 260 on the outlet end of the array 200. The isolation inlets 520 or outlets 540 of the arrays 200 can be fluidly connected in parallel or in series by one or more isolation inlet or outlet manifolds, respectively. In operation, the isolation material is preferably flowed through the isolation inlet 520, into the inlet channel 240 and outlet channel 260, to the isolation outlet 540, forming a first isolation layer between the chamber 222 and the inlet channel 240, and a second isolation layer between the pore channel 224 and the outlet channel 260. The isolation layers are preferably 10 to 20 micrometers thick, but can alternatively be thicker. During isolation material introduction, buffer is preferably simultaneously flowed through the inlet channel 240 and outlet channel 260, preferably in the same direction as isolation material flow, wherein the buffer flow rate preferably controls the thickness of the isolation material layers. Buffer flow is preferably established in the portions of the inlet 320 and outlet channel 260 distal from the pores 220. The buffer flow rate is preferably maintained at laminar flow, but can alternatively have any other suitable flow rate. Alternatively, the isolation inlet 520 and outlet 540 can be fluidly connected to a first and second isolation channel located within the inlet channel 240 and outlet channel 260, respectively, wherein the first and second isolation channel guides isolation material flow. However, any other suitable mechanism that can establish a first and second isolation layer can be used.

Figure 10A:
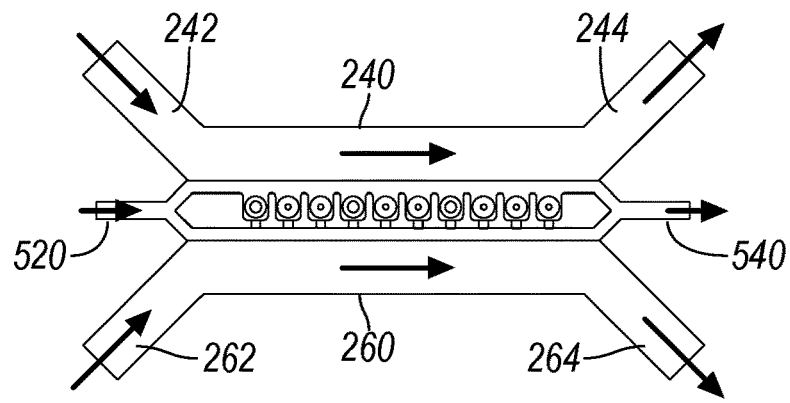
FIGS. 10A, 10B, and 10C are a schematic representation of introducing an isolation material, creating a unique photomask, and selecting for cells of interest, respectively.
Figure 10B:
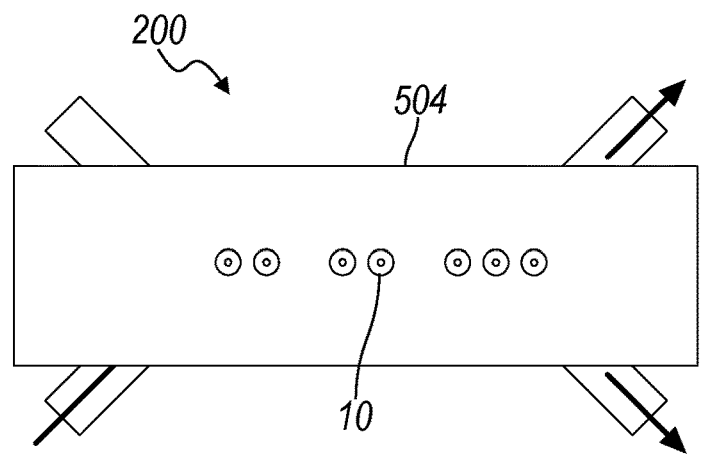
Figure 10C:
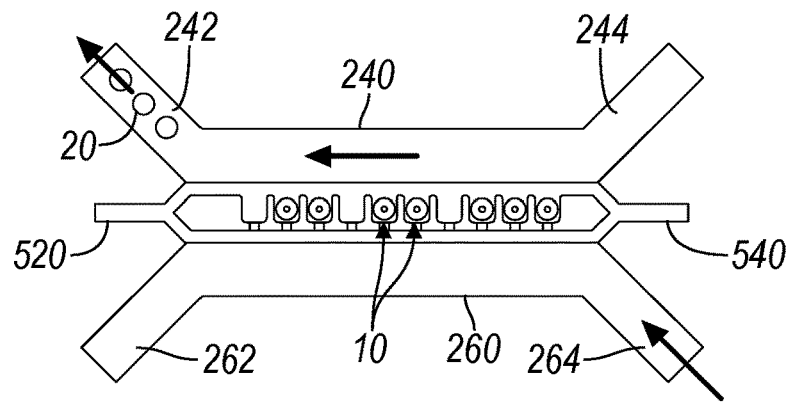

The isolation material preferably isolates a pore 220 within an array 200. The isolation material preferably has a flow state and a set state, wherein a photochemical reaction, thermochemical reaction, polymerization reaction or any other suitable reaction switches the isolation material from the flow state to the set state. In the flow state, the isolation material is preferably substantially viscous, such that the isolation material does not flow into the pores 220 during introduction into the cell capture system 100. In the set state, the isolation material is preferably a solid or gel that prevents cell egress from the pore 220, and is preferably porous or selectively permeable to permit buffer and reagent penetration therethrough. The isolation material is preferably a photopolymerizable hydrogel, such as PEG or polyacrylamide with photoinitiator, but can alternatively be any suitable material with any other suitable polymerization agent. In one variation, the isolation layer may be an immiscible liquid such as oil. In another variation, select portions of the isolation material can be reacted to seal specific pores 220. For example, as shown in FIG. 10B a unique photomask 504 can be created that allows collimated irradiation of isolation material segments blocking pores 220 containing the cells of interest. Photomask 504 may be created by high resolution printing of UV-blocking black ink on a transparency sheet or by use of standard photolithography on photoresist coated glass masks. The selective UV exposure of select regions of the microfluidic chip can also be accomplished by moving a UV laser or a collimated and concentrated UV spot to the select locations using an x-y stage. As shown in FIG. 10C, undesired cells 20 and unreacted isolation material can then be removed from the cell capture system 100 by ingressing fluid through the outlet manifold 400 (e.g. backflowing). Alternatively, the photomask 504 can allow irradiation of isolation material segments blocking pores 220 containing undesired cells 20, wherein desired cells 10 are retrieved from the system. However, any suitable portion of the isolation material can be reacted.

Figure 11A:
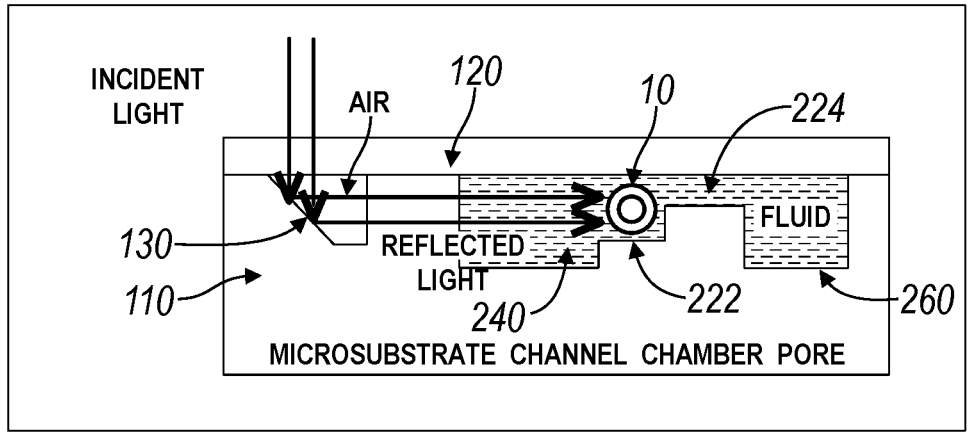
FIGS. 11A, 11B, 11C, and 11D are side views of a first, second, third and fourth optical element, respectively.
Figure 11B:
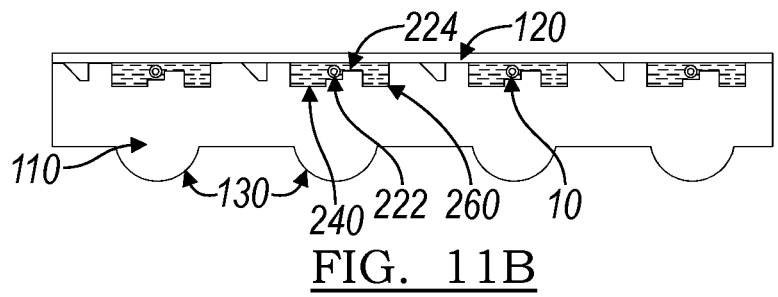
Figure 11C:
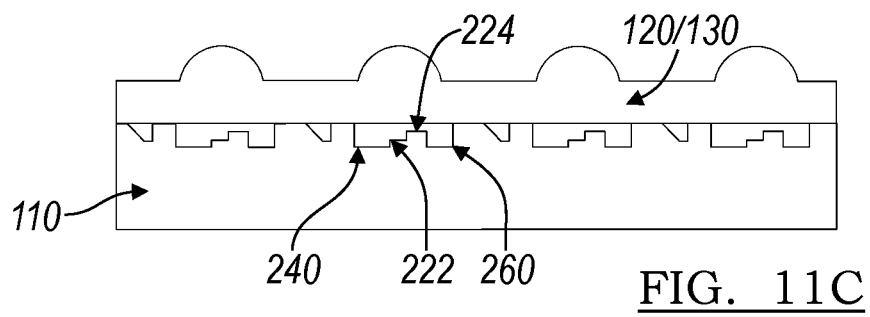
Figure 11D:
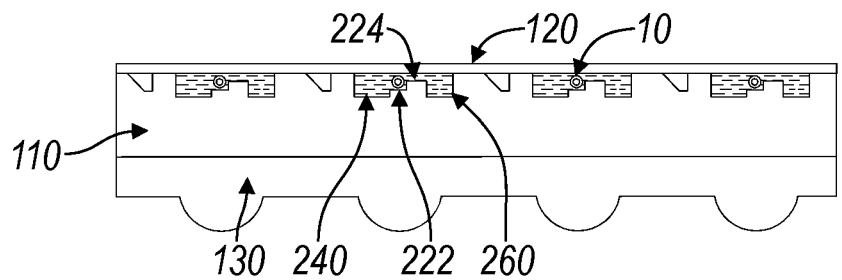
Figure 12A:
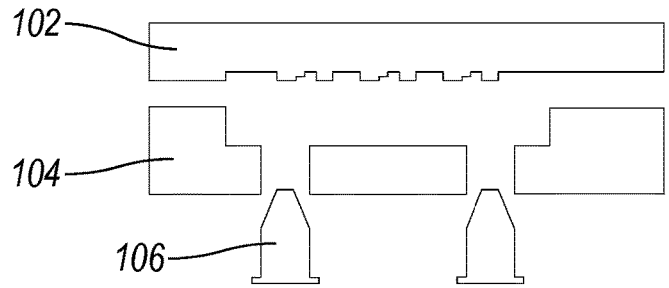
FIGS. 12A, 12B, 12C, 12D, 12E, and 12F is a schematic representation of a method of cell capture system manufacture.
Figure 12B:
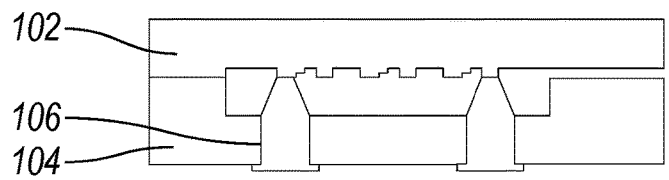
Figure 12C:
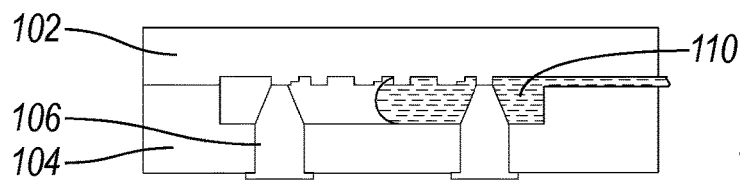
Figure 12D:
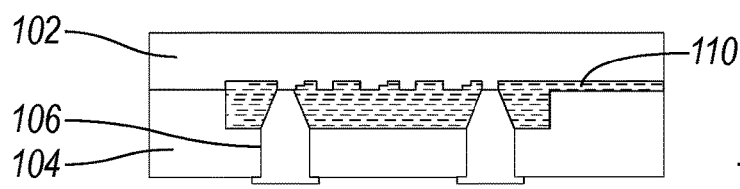
Figure 12E:
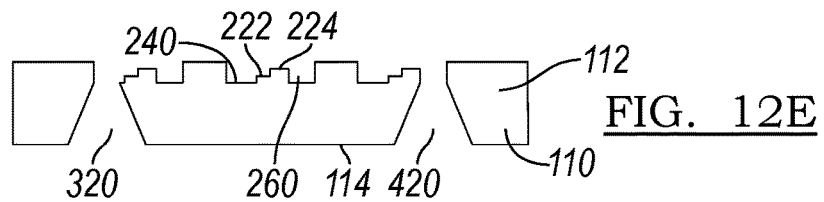
Figure 12F:
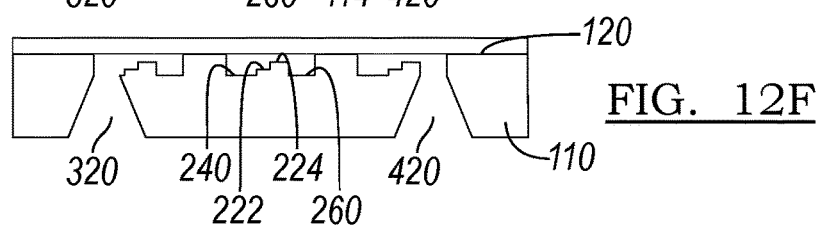

The cell capture system 100 can additionally include optical elements 130 that function to facilitate imaging. The optical elements 130 function to adjust incoming light, preferably to facilitate better imaging. The optical elements 130 can function to bend, reflect, collimate, focus, reject, or otherwise adjust the incoming light. The optical elements 130 are preferably fabricated within the same process as the cell capture system 100 manufacture, but can alternatively be included after cell capture system 100 manufacture. The optical elements 130 are preferably defined within the substrate 110, but can alternatively be defined by the top layer 120 or by a separate component. Optical elements 130 can include light reflectors disposed within the substrate thickness adjacent the arrays 200 (as shown in FIG. 11A), defined on a broad face of the substrate 112 opposite that defining the cell capture system 100 (as shown in FIG. 11B), or microlenses defined on the top layer 120 (as shown in FIG. 11C), light collimators, light polarizers, interference filters, 90° illumination, elements that minimize excitation rays from going into path of collected fluorescence emission light, diffraction filters, light diffusers, or any other suitable optical element. Alternatively, the optical elements 130 can be defined by an imaging stage (as shown in FIG. 11D) or by any external component.

The cell capture system 100 can additionally include pore affinity mechanisms that function to attract a cell of interest 10 towards a pore chamber 222. Pore affinity mechanisms can include electric field traps, features within the inlet channel 240 that direct flow into a pore 220, negative pressure application to the outlet channel 260, or any other suitable pore affinity mechanism.

The cell capture system 100 is preferably defined on a substrate 110. More preferably, the cell capture system 100 is defined on a single broad face of a substrate 112, wherein the array 200, including the inlet channel 240, pores 220, and outlet channel 260, is preferably defined on a single broad face of the substrate 112. More preferably, the array 200, inlet manifold 300, and outlet manifold 400 are all defined on the same broad face. Thus, sample flow through the cell capture system 100 preferably runs substantially parallel to the broad face of the substrate 112. The array 200, inlet manifold 300, and outlet manifold 400 are all preferably defined by recesses in the broad face of the substrate 112, but can alternatively be channels defined by walls that are built on top of the substrate 110, or defined in any other suitable manner. The substrate 110 preferably defines a portion of the cell capture system 100 (e.g. three walls of the system), wherein the remaining portions (e.g. one wall) are preferably defined by a top layer 120. The top layer 120 preferably forms a substantially fluid impermeable seal with the substrate 110 to fluidly seal the cell capture system 100. Alternatively, the cell capture system 100 can be defined through the thickness of the substrate 110, wherein the inlet channel 240 is defined on a first broad face of the substrate 112, the outlet channel 260 is defined on an opposing broad face of the substrate 112, and the pores 220 are defined through the thickness of the substrate 110.

The substrate 110 is preferably optically transparent, biocompatible, and substantially inert. Examples of material that can be used for the substrate 110 include glass, high refractive index polymer, or any other suitable optically transparent material; silicon; any suitable polymer such as polyethlyene, polypropylene, polycarbonate, acrylic, or silicone; quartz, glass, metals, ceramics, or any other suitable material. The top layer 120 is preferably an optically clear layer that is laminated, adhered, heat-bonded, laser-bonded, anodic bonded, or otherwise joined to the substrate 110. The top layer 120 is preferably a polymeric laminate, but can alternatively be a glass cover slip or any other suitable top layer 120.

The cell capture system 100 is preferably manufactured through microfabrication processes, but can alternatively be manufactured through injection molding, a combination of microfabrication (e.g. to create masters) and injection molding (e.g. for bulk manufacturing), a combination of microfabrication (e.g. to create masters) and hot embossing (e.g. for bulk manufacturing), laser etching, CNC, or any other suitable manufacturing process. Microfabrication techniques that can be used include photolithography, DRIE, wet etching, and anodic bonding, but any suitable microfabrication technique can be used. The arrays 200, inlet manifold 300 and outlet manifold 400 are preferably formed within a single manufacturing process, but can alternatively formed through multiple sequential or interrupted processes. The inlet 320 and outlet 420 can additionally be formed within the same process as that of the arrays 200, inlet manifold 300, and outlet manifold 400, but can alternatively be formed before or after using different processes.

In one variation, as shown in FIG. 12, the cell capture system 100 is manufactured using an injection molding process. The injection molding master includes an array-definition portion 102, a bottom-definition portion 104, and one or more core pins 106. The array-definition portion preferably includes the negative for the arrays 200, and can additionally include the negative for the inlet manifold 300 and outlet manifold 400. The array-definition portion is preferably formed using microfabrication techniques, but can alternatively be formed through laser cutting, CNC, or any other suitable method. The bottom-definition portion preferably includes channels through which the core pins can extend. The core pins preferably have tapered ends that insert into the bottom-definition portion channels, and function to define the inlet 320 and outlet 420. The substrate material is preferably injected from an edge of the cell capture system 100 or parallel to the broad face of the to-be substrate 110. However, the substrate material can be injected through the bottom-definition portion, normal to the broad face of the to-be substrate 110, or through any other suitable portion of the master.

In another variation, as shown in FIG. 13, the cell capture system 100 is manufactured using a microfabrication process, and utilizes a series of photolithography steps to create the components of the cell capture system 100 on the substrate 110. However, the cell capture system 100 can be formed using any other suitable method.

Examples of the Cell Capture System

In a first example, as shown in FIG. 4, the cell capture system 100 includes a plurality of substantially identical arrays 200 arranged in parallel; a plurality of inlet manifolds 300, each independently fluidly connected to an inlet channel 240; a plurality of inlets 320, each independently fluidly connected to an inlet manifold 300; a plurality of outlet manifolds 400, each independently fluidly connected to an outlet channel 260; and a plurality of outlets 420, each independently fluidly connected to an outlet manifold 400. Each array 200 preferably includes a plurality of substantially identical pores 220 connected to an inlet channel 240 at the chamber 222 and an outlet channel 260 at the pore channel 224. The arrays 200, inlet manifolds 300, and outlet manifolds 400 are preferably recesses defined on one broad face of a substrate 112, and are preferably cooperatively defined by a top layer 120 that fluidly seals the arrays 200, inlet manifolds 300, and outlet manifolds 400 from the cell capture system 100 exterior. The inlets 320 and outlets 420 are preferably holes defined through the thickness of the substrate 110, and preferably originate from the substrate broad face opposing the face defining the arrays 200, inlet manifolds 300, and outlet manifolds 400. Alternatively, the inlets 320 and outlets 420 can be holes extending through the substrate 110 from the substrate sides.

In a second example, as shown in FIG. 5, the cell capture system 100 includes a plurality of substantially identical arrays 200 arranged in parallel; one inlet manifold 300 including two or more tiers; an inlet 320 fluidly connected to the inlet manifold 300; a plurality of outlet manifolds 400, each independently fluidly connected to an outlet channel 260; and a plurality of outlets 420, each independently fluidly connected to an outlet manifold 400. Each array 200 preferably includes a plurality of substantially identical pores 220 connected to an inlet channel 240 at the chamber 222 and an outlet channel 260 at the pore channel 224. The inlet sub-manifolds 302 directly connected to the inlet channels 240 preferably each independently connect to ten or less inlet channels 240. For example, when the cell capture system 100 includes forty arrays 200, the cell capture system 100 preferably includes ten second tier inlet sub-manifolds 302, each connected to four inlet channels 240. The arrays 200, inlet manifolds 300, and outlet manifolds 400 are preferably recesses defined on one broad face of a substrate 112, and are preferably cooperatively defined by a top layer 120 that fluidly seals the arrays 200, inlet manifolds 300, and outlet manifolds 400 from the cell capture system 100 exterior. The inlet 320 and outlets 420 are preferably holes defined through the thickness of the substrate 110, and preferably originate from the substrate broad face opposing the face defining the arrays 200, inlet manifolds 300, and outlet manifolds 400. Alternatively, the inlet 320 and outlets 420 can be holes extending through the substrate 110 from the substrate sides. Alternatively, the inlet 320 can be a hole defined through the thickness of the substrate 110, while the outlets 420 are holes extending parallel to the substrate broad face through the substrate 110.

In a third example, as shown in FIGS. 7 and 8, the cell capture system 100 includes a plurality of substantially identical arrays 200 arranged in parallel; one inlet manifold 300 including two or more tiers; an inlet 320 fluidly connected to the inlet manifold 300; one outlet manifold 400 including two or more tiers; and an outlet 420 fluidly connected to the outlet manifold 400. Each array 200 preferably includes a plurality of substantially identical pores 220 connected to an inlet channel 240 at the chamber 222 and an outlet channel 260 at the pore channel 224. The outlet manifold 400 preferably has the same number of tiers as the inlet manifold 300, and preferably mirrors the inlet manifold 300. For example, an outlet sub-manifold 402 directly connected to the arrays 200 is preferably connected to the same arrays 200 that a corresponding inlet sub-manifold 302 is directly connected to. However, the outlet manifold 400 can include a different number tiers, group the arrays 200 differently, or have any other suitable configuration. The inlet 320 and outlet sub-manifolds 402 directly connected to the inlet 320 and outlet channels 260 preferably each independently connect to ten or less inlet 320 and outlet channels 260, respectively. For example, when the cell capture system 100 includes forty arrays 200, the cell capture system 100 preferably includes ten second tier inlet 320 and outlet sub-manifolds 402, each connected to four inlet 320 and outlet channels 260, respectively. The arrays 200, inlet manifold 300, and outlet manifold 400 are preferably recesses defined on one broad face of a substrate 112, and are preferably cooperatively defined by a top layer 120 that fluidly seals the arrays 200, inlet manifold 300, and outlet manifold 400 from the cell capture system 100 exterior. The inlet 320 and outlet 420 are preferably holes defined through the thickness of the substrate 110, and preferably originate from the substrate broad face opposing the face defining the arrays 200, inlet manifold 300, and outlet manifold 400. Alternatively, the inlet 320 and outlet 420 can be holes extending through the substrate 110 from the substrate sides. Alternatively, the inlet 320 can be a hole defined through the thickness of the substrate 110, while the outlet 420 is a hole extending parallel to the substrate broad face 112, through the substrate 110.

In a fourth example, as shown in FIG. 8, the cell capture system 100 includes a plurality of different arrays 200 arranged in parallel but fluidly connected in series; one inlet manifold 300 connected to the upstream inlet channel 240; an inlet 320 fluidly connected to the inlet manifold 300; one outlet manifold 400 connected to the downstream outlet channel 260; and an outlet 420 fluidly connected to the outlet manifold 400. The pore channel width of the arrays 200 preferably decreases with each subsequent array 200 away from the inlet 320. Furthermore, the chamber size of the arrays 200 can decrease with each subsequent array 200 away from the inlet 320. The inlet and outlet channel size of the arrays 200 can also decrease with each subsequent array 200 away from the inlet 320. Each array 200 preferably includes a plurality of substantially identical pores 220 connected to an inlet channel 240 at the chamber 222 and an outlet channel 260 at the pore channel 224. The outlet channel 260 of an upstream array 200 is preferably fluidly connected to the inlet channel 240 of the adjacent downstream array 200. In one specific example, the cell capture system 100 includes a first, second, third, and fourth array 200 fluidly connected in series. The first array 200 has a pore channel size of 30 micrometers, the second array 200 has a pore channel size of 25 micrometers, the third array 200 has a pore channel size of 15 micrometers, and the fourth array 200 has a pore channel size of 10 micrometers. The arrays 200, inlet manifold 300, and outlet manifold 400 are preferably recesses defined on one broad face of a substrate 112, and are preferably cooperatively defined by a top layer 120 that fluidly seals the arrays 200, inlet manifold 300, and outlet manifold 400 from the cell capture system 100 exterior. The inlet 320 and outlet 420 can be holes defined through the substrate 110 on the same side of the substrate 110, on the same broad face of the substrate 112, on opposing broad faces of the substrate 110, on adjacent faces of the substrate 110, or arranged in any suitable configuration.

In a fifth example, as shown in FIG. 9, the cell capture system 100 includes a first and a second array set 202, each array set 202 including a plurality of substantially identical arrays 200 arranged in parallel, wherein each array 200 preferably includes a plurality of substantially identical pores 220. The cell capture system 100 preferably includes one inlet manifold 300 fluidly connected to the inlet channels 240 of both array set 202s, but can alternatively include two inlet manifolds 300, each independently connected to an array set 202, or any other suitable number of inlet manifolds 300. In one variation, the inlet manifold 300 can be disposed between the array set 202s, such that the second array set 202 is an enantiomer of the first array set 202. However, the inlet manifold 300 can be disposed in any suitable position. The cell capture system 100 preferably includes one inlet 320, but can alternatively include more. In one variation, the inlet 320 is arranged equidistant between the array set 202s. The cell capture system 100 preferably includes two outlet manifolds 400, one for each array set 202, but can alternatively include a plurality of outlet manifolds 400, one manifold for each outlet channel 260, or any other suitable number of outlet manifolds 400. In one variation, the outlet manifold 400(s) can be disposed proximal the substrate 110 edges, such that the outlet manifold 400(s) for the first array set 202 is arranged on the side of the first array set 202 distal the second array set 202, and the outlet manifold 400(s) are arranged on the side of the second array set 202 distal the first array set 202. The cell capture system 100 preferably includes at least two outlets 420, but can alternatively include more.

In a sixth example, as shown in FIG. 9, the cell capture system 100 is substantially similar to the cell capture system 100 of the fifth example, and can additionally include a third array set 202 including a plurality of substantially identical parallel pores 220 and a retrieval channel 502 fluidly connecting the inlet manifold 300 of the first and second array set 202 with the inlet manifold 300 of the third array set 202. In this example, the third array set 202 can function as a single-cell reactor, wherein each array 200 within the third array set 202 can additionally include an isolation inlet 520 and an isolation outlet 540 for each array 200 within the set, the isolation inlet 520 and outlet 420 disposed between the first and second ends of the inlet channel 240 and outlet channel 260, respectively. In operation, the retrieval channel 502 is preferably sealed proximal the inlet manifold 300, and cells of interest are isolated within the first and second array set 202s by running a sample through the inlet 320, through inlet manifold 300, and into the first and second array set 202s. After cell isolation, the retrieval channel 502 can be unsealed, the inlet 320 sealed, and the isolated cells back-flowed through the inlet manifold 300, through the retrieval channel 502 and into the third array 200 by running a buffer through the outlet manifold 400(s) of the first and second array set 202s. As shown in FIG. 10, the cells can then be isolated from adjacent cells by simultaneously introducing an isolating material, such as hydrogel, into the isolation inlet 520 and a buffer into the first ends of the inlet channel 240 and outlet channel 260. The isolating material is then preferably reacted to switch the isolating material from a flow state to a set state. In one variation, only portions of the isolating material sealing the pores 220 containing the cells of interest are reacted. For example, the isolated cells can be stained, the pores 220 containing the cells of interest identified (e.g. wherein the cells of interest emit a desired wavelength), and a photomask 504 created, wherein the photomask 504 permits only the portions of the isolating material sealing the pores of interest to be photoreacted (e.g. through UV irradiation). Unreacted isolating material and undesired cells 20 can be egressed by backflowing buffer through the outlet manifold 400. However, any other suitable method of selective isolating material reaction can be used. Reagents (e.g. flourogenic antibodies, etc), analytes, or any other suitable substance can be introduced into the third array 200 through the third array inlet 320 prior to cell isolation. Alternatively, reagents can be introduced post cell isolation. In a first variation, the reagents can be introduced through the third array inlet manifold, wherein the reagent penetrates through the set isolating material to ingress into the pore 220. In a second variation, reagents, analytes, or other substances can be introduced into individual pores 220 by introducing the substance through the portion of the top layer 120 contiguous with the pore of interest.

Cell Removal

The cell capture system 100 is configured to facilitate selective cell removal from known, addressable locations. While an individual cell from a single pore 220 is preferably selectively removed, the system can facilitate simultaneous multiple cell removal from a single array 200 or a subset of arrays 200. The cell is preferably removed by applying a removal force to the cell. The removal force is preferably applied by pumping fluid through the pore channel 224 into the chamber 222, but can alternatively be applied by aspirating the contents out of the chamber 222. In one variation, the pump pressure provided by a pump mechanism at the cell capture system 100 outlet 420 is less than 10,000 Pa. In one specific variation, the provided pump pressure is 6,000 Pa. However, any other suitable pump or aspiration pressure can be used.

In a first variation of the cell removal method, one or more cells can be removed from the cell capture system 100 by ingressing a purging fluid through an outlet manifold 400 and collecting flushed-out cells at the inlet 320 (backflowing the cells). This can be particularly desirable when collection of cells from multiple fluidly linked sites is desired. Cell capture system 100s including multiple outlet manifolds 400 (e.g. systems with one outlet manifold 400 per array 200) can be particularly suited to this cell removal method, as the cells within a given array 200 can be removed without affecting adjacent captured cells within other arrays 200 by only ingressing fluid through the outlet manifold 400 directly connected to the selected array 200. Alternatively, cell capture system 100s with multiple tiers of sub-manifolds can be suited to this cell removal method, wherein cells retained within a subset of arrays 200 that are fluidly connected by sub-manifold can be simultaneously removed. However, any suitable cell capture system 100 configuration can be utilized with this cell removal method.

In a second variation of the cell removal method, cell removal can be achieved by utilizing a cell removal tool 600. The cell removal tool 600 of the cell capture system 100 functions to selectively remove one or more isolated cells from an addressable location within the cell capture system 100. The cell removal tool 600 is preferably configured to remove a cell from a single chamber 222, but can alternatively be configured to simultaneously remove multiple cells from multiple chambers 222.

In a first variation of the cell removal tool, the cell removal tool 600 is configured to puncture the top layer 120 from a direction normal to the broad face of the substrate 112. The cell removal tool 600 preferably removes the cell in a substantially normal direction from the broad face of the substrate 112, but can alternatively remove the cell in an angled direction relative to the broad face of the substrate 112. The cell removal tool 600 preferably includes a hollow needle that punctures the top layer 120 and defines a substantially fluidly isolated volume in fluid communication with one or more pores 220 (e.g. the desired number of pores 220). As shown in FIGS. 14A and 14B, the hollow needle preferably includes one or more sealing elements at the tip 620, such as a polymeric coating or adequate geometry, that facilitate fluid seal formation with the top layer 120. The hollow needle preferably includes a cannula ending in a hollow tip 620. The cannula preferably defines a lumen, and is preferably fluidly connected to a cell collection volume. In one variation, the tip 620 includes geometry that facilitates fluid seal formation with the top layer 120. The tip 620 preferably includes a first and second opposing wall, each having concave profiles that taper into a perforating end distal the cannula. The first wall is preferably an enantiomer of the second wall, but can alternatively be substantially identical or different. The first and second sides of each wall (622 and 624, respectively) preferably exhibit different curvatures, such that the center of the perforating end is preferably offset from the longitudinal axis of the lumen. However, the first and second walls can alternatively be substantially similar (e.g. have the same curvature). The first and second opposing walls preferably function to perforate the top layer 120 and to form a first and second fluid seal with the substrate 110 to define the fluidly isolated volume. However, the hollow needle can include any other suitable geometry. In one variation, the hollow needles have a height of 200 micrometers and a lumen diameter of 40 micrometers.

The hollow needle is preferably configured to form a substantially fluidly isolated volume within a pore chamber 222 of interest or a segment of the inlet channel 240 adjacent a pore chamber 222 of interest. A low-pressure generator (e.g. a pump) is preferably then used to aspirate the retained cell out of the pore chamber 222, through the hollow needle, and into the cell collection volume.

The hollow needle is preferably manufactured using microfabrication techniques, but can alternatively be injection molded, laser cut, stamped, or manufactured using any other suitable manufacturing technique. In one variation of hollow needle manufacture, as shown in FIG. 15, a lumen is preferably etched into a substrate 110, such as silicon, using etching techniques such as deep reactive ion etching (DRIE), plasma etching, or any other suitable etching method. This step is preferably utilized with a mask that covers the portions of the substrate 110 to be protected. The walls and associated profiles are then preferably manufactured through isotropic etching of the substrate 110 utilizing a corrosive liquid or plasma, but any other suitable isotropic material removal method can be used. A mask is preferably used to protect the puncture end. Multiple hollow needles are preferably simultaneously manufactured as an array 200, but can alternatively be individually manufactured.

In a second variation of the cell removal tool, the cell removal tool 600 is also configured to puncture the top layer 120 from a direction normal to the broad face of the substrate 112. The cell removal tool 600 preferably removes the cell in a substantially normal direction from the broad face of the substrate 112, but can alternatively remove the cell in an angled direction relative to the broad face of the substrate 112. As shown in FIG. 16, the cell removal tool 600 preferably includes a hollow needle pair including a first needle 640 and a second needle 660, wherein both needles are preferably substantially similar to that described in the first variation of the cell removal tool 600. The first and second walls of the first needle 640 are preferably configured to form a first and second fluid impermeable seal with the inlet channel 240 and/or the pore chamber 222. The first and second walls of the second needle 660 are preferably configured to form a first and second fluid impermeable seal with the outlet channel 260 and/or pore channel 224. The first and second needles are preferably aligned in parallel, with the perforating tips of the first and second needles adjacent and oriented in the same direction within the cell removal tool 600 (e.g. wherein both tips are located on the same side of the cell removal tool 600). The first and second needles are preferably manufactured using the aforementioned manufacturing process, but can alternatively be manufactured using different processes. The first and second needles are preferably simultaneously manufactured on the same substrate 110, but can alternatively be separately manufactured and joined post-manufacture. The distance between the first and second needle 660 is preferably substantially equivalent to the pore 220 length (e.g. the sum of the chamber 222 and pore channel 224 lengths). However, the distance between the first and second needle 660 can be the chamber length, the pore channel 224 length, or any suitable distance. The first and second needles 660 preferably cooperatively form a fluidly isolated volume, the fluidly isolated volume including one or more pores of interest, segment of the inlet channel 240 adjacent the pore(s) of interest, and segment of the outlet channel 260 adjacent the pore(s) of interest, such that the pore(s) of interest are fluidly isolated from adjacent pores 220. In operation, fluid is preferably ingressed through the second needle 660 into the fluidly isolated segment of the outlet channel 260, through the pore channel 224, through the chamber 222, and into the first needle 640. As the fluid moves through the chamber 222, the fluid preferably entrains the retained cell and moves the cell into the first needle 640. The second needle 660 can be fluidly coupled to a pump and a fluid source. Alternatively/additionally, the first needle 640 can be fluidly coupled to a low-pressure generator (e.g. a pump). The fluid is preferably a buffer, but can alternatively be cell culture media or any other suitable fluid that retains cell viability.

Figure 17A:
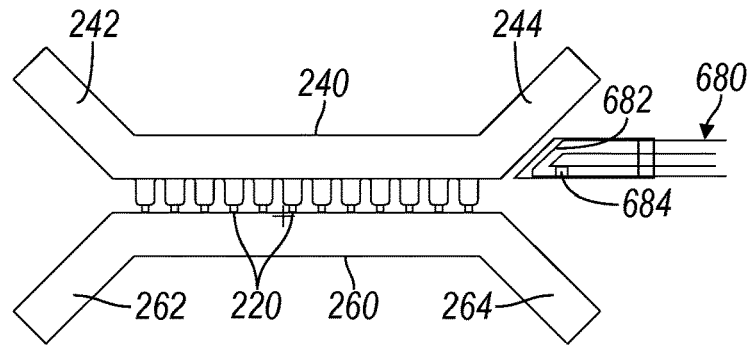
FIGS. 17A and 17B are schematic representations of a second variation of cell removal, including cell of interest identification and cell removal tool alignment with the pore containing the cell of interest, respectively.

In a third variation of the cell removal tool, the cell removal tool 600 is configured to remove one or more cells from the cell capture system 100 in a direction substantially parallel to the broad face of the substrate 112. As shown in FIG. 17, the cell removal tool 600 preferably includes a cannula 680 defining a lumen and an aperture 684. The cannula 680 preferably terminates in a sealed puncture tip 682 at a first end, and is preferably fluidly connected to a cell collection volume at a second end. The aperture 684 is preferably a hole that extends through the cannula 680 wall, wherein the hole preferably has a width substantially equivalent to or larger than the width of a pore chamber 222, but small enough such that the aperture 684 does not span two pore chambers 222. The cannula 680 preferably includes one aperture 684, but can alternatively include multiple apertures 684, wherein the multiple apertures 684 can be aligned in a line parallel to the longitudinal axis of the cannula 680, or can be distributed about the surface of the cannula 680 (e.g. spiral about the longitudinal axis of the cannula 680). The aperture 684 preferably extends through a longitudinal cannula 680 wall, but can alternatively extend through a portion of the puncture tip 682. In one example, the aperture 684 extends through a portion of the longitudinal cannula wall proximal the puncture tip 682. In another example, the aperture 684 extends through a portion of the longitudinal cannula wall a predetermined distance from the puncture tip 682, wherein the distance can be configured such that the cannula wall blocks one or more of the adjacent pores 220. In another example, the aperture 684 can extend through the puncture tip 682 such that the longitudinal axis of the aperture 684 extends in parallel or coaxially with the longitudinal axis of the cannula 680. The transition between the aperture 684 and the cannula 680 exterior and/or interior is preferably convex and curved to prevent cell damage, but can alternatively be concave, angled, be at right angles, or have any suitable configuration. The cannula 680 preferably has a circular cross section, but can alternatively have a rectangular or square cross section, ovular cross section, or any other suitable cross section. The cannula 680 is preferably rigid, but can alternatively be flexible or include flexible portions. In one alternative, the cannula 680 is flexible and includes a rigid puncture device 686, wherein the rigid puncture device 686 is slidably coupled over the cannula 680. The rigid puncture device 686 forms and retains an entryway into the inlet channel 240, and the cannula 680 can be advanced therethrough. However, the cannula 680 can have any other suitable configuration. The cannula 680 can additionally include a perforator slidably coupled within the lumen, wherein the perforator can extend through the aperture 684 to perforate any intermediary layers between the cannula 680 and the pore 220 (e.g. an isolation layer). The perforator position post perforation can be retained to facilitate cell removal therethrough, or the perforator can be retracted prior to cell removal.

In one variation of cell retrieval tool operation, the cannula preferably traverses through the inlet channel 240 of an array 200 having a cell of interest 10 until the aperture is aligned with the pore 220 containing the cell of interest 10. Fluid can then be ingressed through the associated outlet manifold 400, wherein the pressure of the ingressed fluid pushes the cell of interest 10 out of the pore chamber 222, through the aperture, and into the cannula. Subsequent fluid ingress through the inlet channel 240 can recapture any cells that were backflowed out of their respective pores 220. The cannula can additionally or alternatively include a low-pressure generation mechanism fluidly coupled to the lumen that aspirates the cell out of the pore 220. Alternatively or additionally, the cannula can facilitate cell ingress through capillary action. The cell preferably travels through the lumen and is stored within the cell collection volume.

Figure 17B:
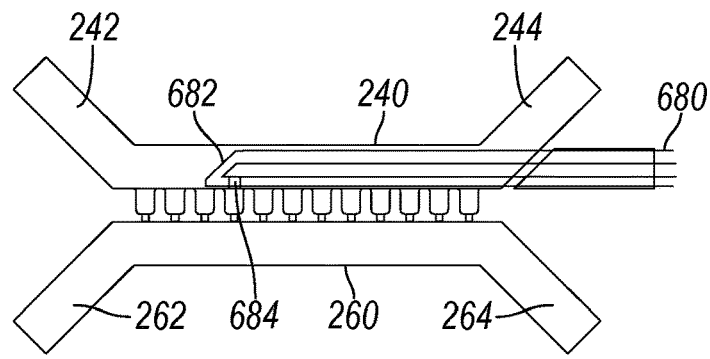

In this variation of cell retrieval tool operation, the cannula is preferably inserted into the inlet channel 240 through the side of the substrate 110, as shown in FIG. 17B, wherein the inlet channel 240 preferably partially defined by a self-sealing wall. The cannula is preferably extended through this self-sealing wall. Alternatively, the cannula can be inserted into the inlet channel 240 through the top layer 120, wherein the cannula can be flexible to accommodate the angle of entry, or the top layer 120 can be elastic to accommodate the angle of entry. However, any other suitable method of introducing the cannula into the inlet channel 240 can be used.

In another variation of cell retrieval tool operation, the cannula includes an aperture through the puncture tip. The cannula is advanced through the inlet channel 240, successively blocking each successive pore chamber 222 until only the desired subset of pores 220 are left uncovered. Fluid can then be provided through the outlet channel 260 directly fluidly connected with the uncovered pores 220 to simultaneously release the cells from the uncovered pores 220, wherein the fluid preferably entrains the cells and moves the cells into the cannula. The cannula can additionally or alternatively be fluidly connected to a low-pressure generator to aspirate the cells into the cell collection volume.

Cell removal from the cell capture system 100 is preferably automated, but can alternatively be semi-automated or manual. In one variation, cell removal is automated, wherein an integrated platform 30 identifies and removes the cells of interest. Cell identification can include automatic fixing, permeabilzation, staining, imaging, and identification of the cells through image analysis (e.g. through visual processing with a processor, by using a light detector, etc.). Cell removal can include advancement of a cell removal tool 600 to the pore 220 containing the cell of interest 10. Cell removal can additionally include cell removal method selection and/or cell removal tool selection. In another variation, cell identification can semi-automated, and cell retrieval can be automated. For example, cell staining and imaging can be done automatically, wherein identification and selection of the cells of interest can be done manually. In another variation, all steps can be performed manually. However, any combination of automated or manual steps can be used.

Example Applications

The cell capture system 100 described above can be used for a variety of biological assays and procedures. Running an assay or procedure preferably includes capturing target cells in addressable locations within the cell capture system and delivering reagents to the interior or surface of each captured cell while maintaining cell registration with its respective pore or location.

Figure 18:
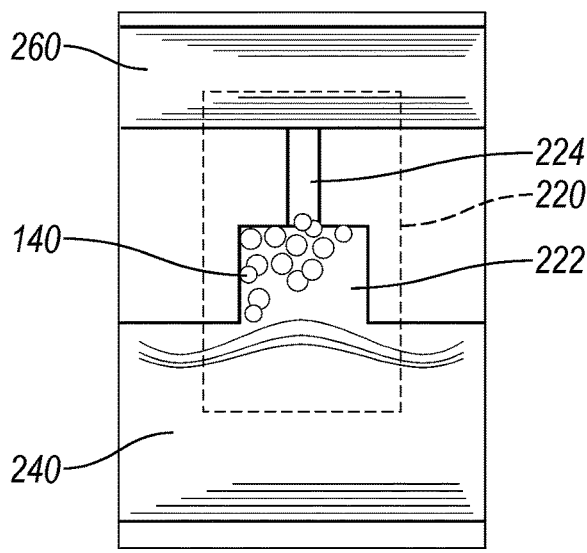
FIG. 18 is a top view of a pore including a variation of microspheres.

In a first example, the cell capture system 100 can be used as a microarray 200, wherein microspheres 140 are introduced into the cell capture system 100 prior to sample introduction. The microspheres 140 are preferably slightly larger than the pore channels 224, but can alternatively be smaller. The microspheres 140 can be coated with specific analytes (e.g. affinity molecules, etc.), wherein the microspheres 140 can create affinity columns within the pores 220. The microspheres 140 can additionally be tagged for imaging. In one variation, multiple sets of microspheres 140 are sequentially introduced into the cell capture system 100, wherein each set of microspheres 140 has an affinity molecule coating different from the other sets. Each microsphere set is preferably tagged with the same imaging tag (e.g. all tagged with Cal Red), but can alternatively be tagged with different imaging tags. Each microsphere set preferably includes a small number of microspheres 140 (e.g. less than the number of pores 220 in the system), but can alternatively have more. The cell capture system 100 is preferably imaged after each microsphere set is introduced to identify the pores 220 occupied by the constituent microspheres 140 of the set. However, the cell capture system 100 can be imaged after all the microspheres 140 are introduced, particularly when each microsphere set is tagged with a different image tag. In this way, a highly multiplexed bead microarrays 200 can be created within the cell capture system 100. In another variation, as shown in FIG. 18, the microspheres 140 can form small pore networks within the pores 220 that functions as a smaller pore filter devices. For example, microspheres 140 of approximately 10 microns can be used to create a bacteria filter, while microspheres 140 of approximately 2 microns can be used to create a virus filter. In another example, affinity molecule-coated microspheres can be introduced contemporaneously with the sample, wherein the microspheres bind with the target cells to form complexes. The microspheres are preferably sized such that the complexes are trapped within the pores while unbound microspheres flow through the system. The microspheres 140 can be polymeric, metallic, paramagnetic, magnetic, or have biological properties. For example, the microspheres 140 can be made of thermally conductive materials and can function as rapid heat exchanger units.

In another example, one or more assays can be run within the cell capture system 100. The cells of interest are preferably first isolated by running the sample through the cell capture system 100. The captured cells are preferably then stained, wherein staining preferably maintains the cell viability. Cell analysis, including morphology and cell counting, is then preferably performed. One or more assays can then be performed on the captured cells. These assays may include Immunocytochemistry, Fluorescence In-situ Hybridization (FISH), Polymerase Chain Reaction (PCR), Enzyme Linked Immunosorbent Assay (ELISA) and other standard cellular and molecular assays known to a person skilled in the art.

Isolating the cells of interest preferably includes pumping the sample through the cell capture system inlet 320 and egressing the remainder of the sample through the cell capture system 100 outlet 420. Isolating the cells of interest can additionally include sample enrichment prior to sample ingress into the cell capture system 100. Isolating the cells of interest can additionally include running a buffer through the cell capture system 100 to rinse the isolated cells. Isolating the cells of interest preferably includes leaving the cells within the pores 220, but can alternatively include cell removal from the cell capture system 100. The removed cells can be passed through a second cell capture system 100 to sequentially enrich the isolated cell population, or can be stored within a cell collection volume for off-chip analysis.

Antibody staining is preferably used to identify the pores 220 that contain the cells of interest. Antibody staining can additionally distinguish the cells of interest over undesired cells 20 of similar size that have also been captured. Antibody staining preferably includes introducing a solution of conjugated antibodies, specific to the cell of interest 10, through the cell capture system 100. The conjugated antibodies are preferably primary antibodies, but can alternatively be secondary antibodies, wherein unconjugated primary antibodies are preferably introduced into the cell capture system 100 prior to conjugated antibody introduction. However, any suitable cell staining method can be used.

Cell analysis is preferably used to determine the morphology of the captured cells and to determine the number and location of captured cells of interest. Cell analysis is preferably performed by an associated integrated platform 30, wherein morphology and cell counting is preferably accomplished through global chip imaging and image analysis. Imaging and analysis is preferably automatically performed, but can alternatively be semi-automated or manually performed. However, morphology determination and cell counting can be achieved through any other suitable method.

Running assays on the isolated cells functions to determine characteristics of the cells and/or determine cell responses to given stimuli. Analyses can be run on the cells individually (e.g. single cell level analysis), wherein cells can be individually fluidly isolated within the cell capture system 100. Alternatively, analyses can be run on the cell capture system 100 as a whole. Alternatively, individual array 200 subsets can be fluidly isolated from other array 200 subsets, wherein different analyses can be performed on different array 200 subsets. Example assays that can be run on the cells include FISH assays, selective cell lysing and lysate collection, single cell molecular analysis (e.g. PCR, RT-PCR, Whole Genome Amplification, ELISPOT, ELISA, Immuno-PCR, etc.), drug testing, cell culturing, affinity analyses, time-responsive analyses, but other analyses can alternatively/additionally be run. Isolated cells can be removed prior to, during, or after the assays have been run, preferably with the cell removal tool 600 but alternatively with any suitable method. Alternatively, isolated cells can be isolated within the chamber 222 (e.g. with an isolation layer), fixed, cultured within the chamber 222, or be retained within the chamber 222 in any other suitable manner.

In one specific example, assaying cells with the cell capture system 100 includes pre-processing a sample containing spiked cancer cells, priming the cell capture system 100, flowing the sample through the cell capture system 100, fixing the cells within their respective pores, and staining the fixed cells. After the assaying procedure, the cells can be manually or automatically imaged and analyzed. The sample is preferably a peripherial whole blood sample, but can be any other suitable sample containing target cells. The cell capture system 100 preferably includes 12,800 pores, but can alternatively include more or less pores. Pre-processing the sample preferably includes diluting the sample (e.g. with a 0.5% formalin in 1× PBS mixture or any other suitable solution containing a fixing agent) and incubating the sample, preferably in a rocker (e.g. for 15-30 minutes). Priming the cell capture system 100 preferably includes introducing an initial buffer (e.g. 1% BSA+0.1% triton X in 1× PBS) and removing air bubbles from the system 100. Flowing the sample through the cell capture system 100 preferably includes flowing the sample through the system 100 at a pressure of less than 10,000 Pa in less than 10 minutes while minimizing the introduction of air bubbles, but can alternatively include flowing the sample through the system 100 at any suitable pressure in any suitable time frame. Fixing the cells preferably includes post fixing the cells with a fixing agent (e.g. 2% formalin in wash buffer), which can prepare the cells for subsequent antibody staining. Staining the fixed cells can include washing the fixed cells (e.g. with 1% BSA+25 mM EDTA in 1× PBS) and introducing an antibody cocktail containing antibodies specific to the cells of interest (e.g. a primary antibody cocktail including anti-cytokeratin 8/18 or anti-EpCAM that recognize human epithelial cancer cells, $CD_{45}$ that recognizes leukocytes, and/or nuclear stain Hoescht 33342) into the cell capture system 100. Staining the fixed cells can additionally include incubating the cells (e.g. for 30-45 minutes at room temperature). Staining the cells can additionally include washing the cells with a wash buffer (e.g. 1% BSA+25 mM EDTA in 1× PBS), introducing a secondary antibody cocktail containing antibodies that bind to the primary antibodies (e.g. a cocktail including Alexa-conjugated anti-$CD_{45}$, anti-cytokeratin 8/18, and/or anti-EpCAM), and incubating the cells (e.g. at room temperature for 45 minutes). Assaying the cells can additionally include wash steps between each assay step. The cells are preferably washed with a wash buffer including culture media, buffer, metal ion scavengers and/or surfactants (e.g. a wash buffer including 1% BSA and 0.1% triton X in 1× PBS, a wash buffer including EDTA, etc.).

Sample Preparation

The cell capture system 100 is preferably used with a cell-containing sample. The cell-containing sample is preferably a blood sample, but can alternatively be bodily fluid, cells suspended in buffer or culture medium, or any other suitable cell-containing sample.

While the cell-containing sample can be introduced into the cell capture system 100 without any pre-processing, pre-processing can be preferred to increase the efficacy of cell sorting. Sample pre-processing preferably includes sample enrichment to increase the proportion of desired cells 10 within the sample. Sample enrichment preferably includes substantially removing undesired components from the sample before sample ingress into the cell capture system 100. Sample pre-processing can additionally include preparing the sample for downstream processing or processing the sample in any other suitable manner for any suitable application.

In a first variation, sample components that can form obstacles, such as clots, within the cell capture system 100 are preferably removed. For example, in a blood sample, such components can include red blood cells, platelets, and other similar blood components. These components are preferably removed through density gradient centrifugation, wherein the erythrocyte and granulocyte pellet is preferably discarded, and the remainder of the sample retained. However, these components can be removed through filtration, selective lysing, or any other suitable method of removal or inactivation.

In a second variation, undesired cells 20 of substantially the same size as the desired cells 10 are selectively removed. For example, if CTCs are the desired cells 10, then mononuclear cells (e.g. PMBCs) are preferably removed. Undesired, similarly-sized cells are preferably removed by negative selection, but can alternatively be removed by other suitable removal methods, such as centrifugation. Negative selection is preferably achieved through immunomagnetic separation of undesired cells, wherein antibody-coated magnetic particles are introduced into the sample. The antibodies coating the magnetic particles are preferably targeted toward antigens expressed by the undesired cells 20 but not expressed by the desired cells 10. For example, if leukocytes are the undesired cells 20, then anti-$CD_{45}$ can be used. The sample is then passed through a magnetic field, wherein the magnetic particles selectively remove the bound, undesired cells 20 from the sample.

Negative selection can alternatively or additionally be achieved within the cell capture system 100, wherein the cell capture system 100 includes a first stage fluidly connected to a downstream a second stage. The channels of the first stage preferably include affinity molecules (e.g. antibodies) that selectively bind the undesired cells 20, while permitting the desired cells 10 to flow therethrough. The affinity molecules can be introduced as a coating, as affinity molecule-coated microspheres 140, affinity molecule-coated micropillars, affinity molecule-coated microchannels, or introduced in any other suitable manner. The first stage can be a portion of the inlet manifold 300 or a subset of upstream arrays 200, a separate cell capture system 100, or any suitable upstream stage. The first stage preferably includes large pore channel size s, preferably larger than the diameter of the desired cell 10 (e.g. 35-50 micrometers). The second stage preferably selects for the desired cell 10 according to cell size and/or deformability, and preferably does not include any antibodies or cell-binding coatings.

In one variation of sample preparation, as shown in FIG. 19, the sample is prepared by removing small sample components through density gradient separation S100 and removing mononuclear cells through immunogenic separation S200. The cells of interest are then isolated using the cell capture system S300, and subsequent assays are performed on the isolated cells S400.

Integrated Platform

As shown in FIG. 20, the cell capture system 100 is preferably utilized with an integrated platform 30 including a sample workstation 40 and an imaging platform 50. The integrated platform 30 is preferably fully automated, but can alternatively be semi-automatic or manually operated. The integrated platform 30 can perform all or some the functions of pipetting, aliquoting, mixing, pumping, and monitoring. The integrated platform 30 can additionally automatically identify occupied chambers 222, image said chambers 222, and/or perform analyses on said chambers 222. The integrated platform 30 can additionally selectively remove cells from the cell capture system 100. The integrated platform 30 can additionally or alternatively perform any other suitable function. The cell capture system 100 is preferably utilized with a cell capture system 100 as described above, but can alternatively be utilized with any suitable apparatus or method.

The sample workstation 40 preferably includes a pumping system that regulates the sample flow rate through the system to control the shear forces on the cells while providing enough positive pressure to push unwanted cells and fragments through the pore chambers 222 of the pores 220. In one variation, the pumping system provides a pumping pressure less than 10,000 Pa. More preferably, the pumping system provides a pumping pressure of approximately 6,000 Pa, but can alternatively provide any suitable pumping pressure. The pumping system is preferably capable of handling varying volume inputs, preferably ranging from 100 microliters to tens of milliliters. As shown in FIG. 21, the pumping system preferably couples to the inlet 320 and outlet 420 of the cell capture system 100 through a fluidic manifold 42, wherein the fluidic manifold 42 preferably introduces fluid into the cell capture system 100 from above, but can alternatively introduce fluid into the cell capture system 100 from below, from the side, or from any suitable direction. The fluidic manifold 42 preferably includes fluid seal-forming elements 43 about the inlet- and outlet-contacting portions, such as O-rings, gaskets, or any other suitable sealing element. The sample workstation 40 preferably includes a venting system to vent air bubbles (e.g. using hydrophobic vents). The sample workstation 40 can additionally function to prepare the sample for use with the cell capture system 100. For example, the sample workstation 40 can mix reagents, facilitate unwanted cell removal from the sample, or perform any other suitable function. The sample workstation 40 can additionally function to retrieve captured cells, and can include the cell collection volume and the low-pressure generator, if used.

Figure 22:
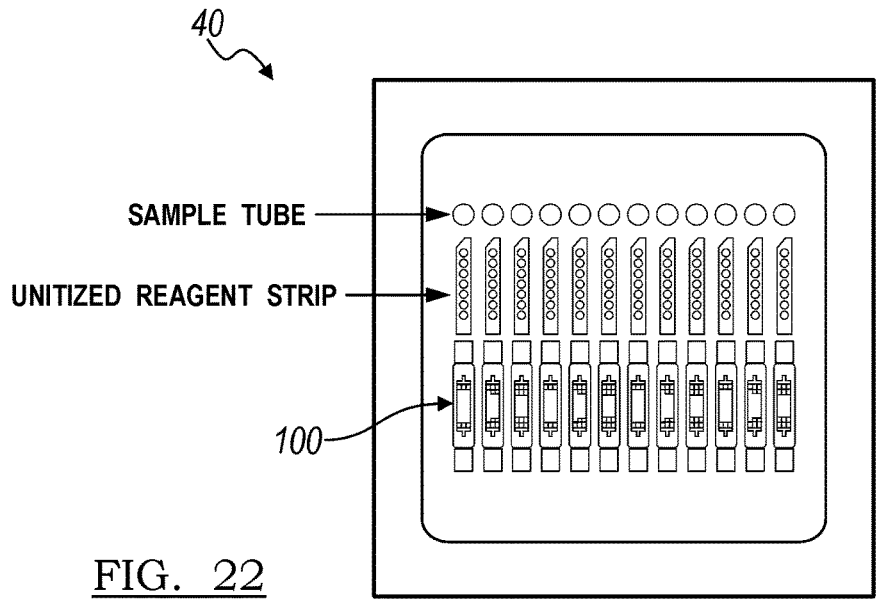
FIG. 22 is a schematic representation of a sample workstation.

The workstation preferably enables simultaneous processing of multiple samples (e.g. 12, 24, 96 samples, etc.) of blood or any other suitable specimen. As shown in FIG. 22, the sample workstation 40 can additionally include predetermined sample locations, wherein sample tubes, such as specimen tubes, can be loaded into a specific location for positive identification throughout the process. Specimen tubes can include unique identifiers (e.g. barcodes) that can be automatically identified by the workstation or manually read. The sample workstation 40 can additionally accept reagents used to process the sample and/or captured cells. The reagents are preferably provided as a unitized reagent strip containing pre-loaded or partially loaded reagents, but can alternatively be provided as separate vials or in any other suitable form factor. Reagents can include wash buffers, purge liquids, cell staining reagents, cell fixing reagents, cell growth media, cell lysing reagents, reagents required for in-situ hybridization, reagents required for specific nucleic acid amplification (e.g. PCR reagents), reagents required for blocking the function of specific moieties, reagents required for cleaning the cell capture system 100, or any other suitable reagent. The configuration of reagents on the strip and/or order of reagent provision or arrangement is preferably dependent on the processes desired. The workstation preferably accepts reagents for multiple processes, wherein multiple processes can be simultaneously performed on a single chip. Examples of processes that can be performed include immunostaining, single cell proteomic analysis, nucleic acid analysis, genomic sequencing, or a comparison between the expressed cell RNA and the background plasma expression, testing the efficacy of pharmaceutical agents. The sample workstation 40 is preferably controlled by an independent processor, but can alternatively be controlled by any suitable control mechanism.

The integrated platform 30 can additionally include an imaging platform 50. The imaging platform 50 can function to capture images of cells. The digital imaging system can additionally include software that can allow for specific image quantization and reporting in the platform. The imaging platform 50 preferably includes imaging hardware and imaging software. The imaging software preferably controls the imaging hardware, and can additionally process the images. In one variation, the imaging software analyzes a first image to determine addresses of the pores 220 retaining cells of interest, then controls the imaging hardware to individually image and interrogate each identified pore 220. The imaging software can additionally store the location of the cells of interest for further cell processing, such as cell removal or single cell analysis.

The imaging hardware is preferably configured to accept the cell capture system 100, and can additionally accept conventional imaging equipment, such as microscope slides, cell culture plates, or any other suitable imaging equipment. The imaging hardware is preferably capable of auto-focusing the microscope before image capture, but can alternatively take a series of images at multiple focal lengths, use image post-processing to sharpen the image, or utilize any other suitable method to achieve a focused image.

The imaging hardware preferably includes an automated stage 52 that can facilitate self-calibration, cell capture system interrogation, cell capture system 100 agitation, or move the imaging equipment in any other suitable manner. The automated stage 52 can additionally function to align the cell capture system 100 with the objective or field of image. The automated stage 52 can additionally move the cell capture system 100 relative to the cell removal tool 600 to align the cell removal tool 600 aperture with a desired pore 220. The automated stage 52 can additionally move the cell to the sample workstation 40. The automated stage 52 is preferably driven by a motor, but can be driven by any other suitable mechanism.

Figures 23A, 23B, 23C:
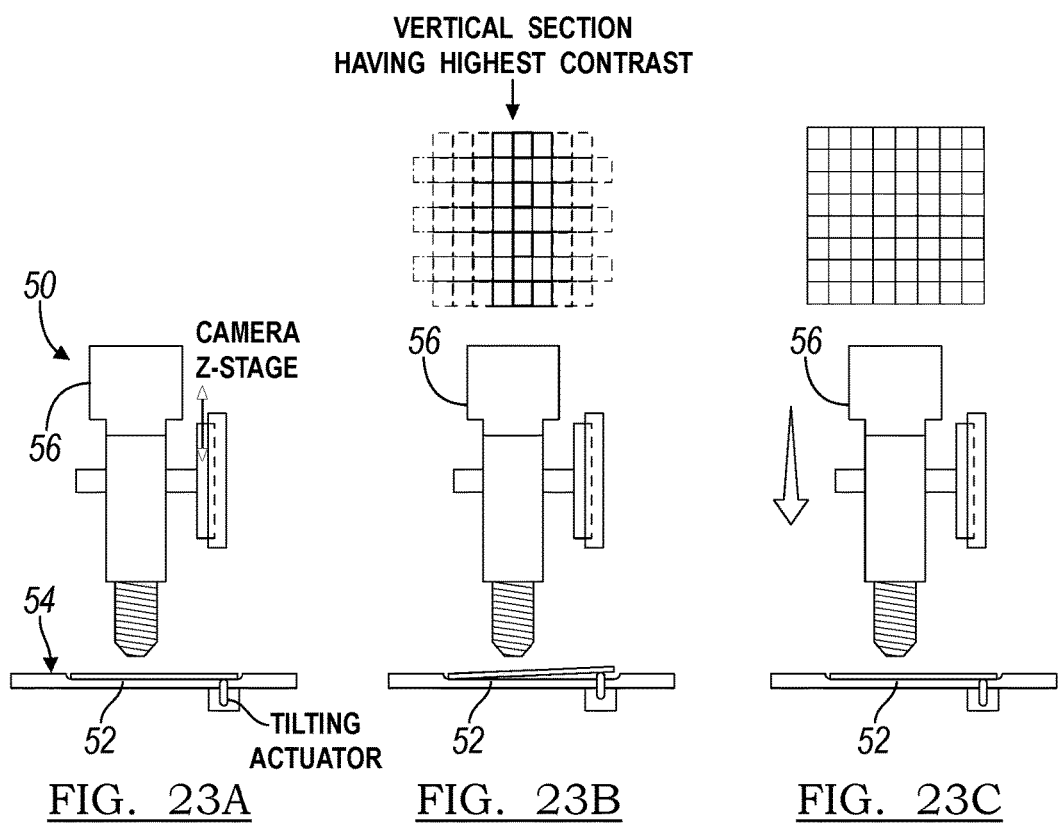
FIGS. 23A, 23B, and 23C are schematic representations of a method of automated focusing.

The automated stage 52 is preferably capable of moving in at least the z-direction, and can additionally move in the x-direction and/or y-direction. In one variation, as shown in FIG. 23, the stage is additionally capable of tilting the cell capture system 100, which can enable imaging module 56 autofocus. The cell capture system 100 can be tilted at a specified angle, wherein some areas of the slide image will be in better focus than others based on the different resultant focal lengths. The contrast differences created are then interrogated by a computer algorithm that determines the vertical section with the greatest contrast, a measure indicative of the ideal focal length (optimal z-height). The automated stage 52 then replaces the cell capture system 100 to a flat position parallel the base, and move the cell capture system 100 to the determined optimal z-height.

The stage preferably includes a retention mechanism 54 that retains the cell capture system 100 position relative to the rest of the stage. The retention mechanism 54 is preferably further capable of retaining other imaging equipment, such as glass slides or cell culture plates. The retention mechanism 54 can be as a clip that biases the cell capture system 100 against a brace, a recess in a broad face of the stage, or any other suitable retention mechanism 54. The stage preferably accommodates one cell capture system 100 at a time, but can alternatively accommodate multiple cell capture system 100s simultaneously. In one variation, the stage includes a carousel or conveyor tray that includes a plurality of cell capture system 100s, wherein the stage rotates successive cell capture system 100s under the imaging module 56.

The stage can additionally include a thermal control system thermally coupled to the portion of the stage configured to contact the cell capture system 100. The thermal control system can be used to control the cell capture system 100 temperature by heating and/or cooling the cell capture system 100 during assays or reactions. For example, the thermal control system can heat the cell capture system 100 to incubate the cells retained therein, and cool the cell capture system 100 to quench given biochemical reactions. In one variation, the thermal control system includes a single block configured to contact an entire broad face of the cell capture system 100. In another variation, the thermal control system includes multiple sections, each section configured to heat or cool a given portion of the cell capture system 100 broad face. The thermal control system preferably includes electric heaters, but can alternatively include inductive heaters, ceramic heaters, or any other suitable heaters. The thermal control system can include a heat sink, heat pump, heat exchanger, or any other suitable passive or active cooling mechanism. The thermal control system is preferably optically transparent, but can alternatively have any other suitable optical property.

The stage can additionally include a fluidic manifold 42 that interfaces with the inlet 320 and outlet 420 of the cell capture system 100, such that real-time flow through the cell capture system 100 can be visualized.

The imaging hardware preferably additionally includes an imaging module 56 including an imager and an optimized illuminator capable of capturing high-resolution images at multiple predefined locations of the slide and/or global images of the slide. The imaging module 56 is preferably capable of working with various sets of emission and excitation wavelengths, such that the imaging platform 50 can resolve multiple markers (e.g. fluorescent markers, stains, etc.). The illuminator is preferably capable of providing the appropriate illumination and wavelengths for fluorescence resolution, phase contrast microscopy, darkfield microscopy, bright-field microscopy, and/or any other suitable imaging technique. For example, the imaging hardware can include one or more emitters capable of resolving fluorescence dyes such as FAM, Cal Red, Texas Red, Cy5, Cy5.5, or any other suitable fluorescence dye used in cell analysis. The imaging module 56 preferably includes an imager that is preferably optically connected to a microscope that magnifies the portion of the cell capture system 100 to be imaged. The imager can be 5 megapixel, 10 megapixel, 20 megapixel, 50 megapixel, 100 megapixel, or any suitable size imager. The imager can be a CCD, CMOS imager, line scanner, or any other suitable imager.

The imaging hardware can additionally include an identifier reader that functions to read and identify imaging equipment identifiers. The imaging hardware can include a barcode reader, a RFID tag reader, a QR code reader, a nearfield communication device, or any other suitable mechanism that can identify a unique identifier located on the imaging equipment (e.g. the cell capture system 100, a microscope slide, etc.). Alternatively or additionally, the imaging module 56 can be used as the identifier reader. In one variation, a given objective lens is placed over the unique identifier to obtain the correct aspect ratio for imaging module 56 imaging. In another variation, the unique identifier can be pieced together from multiple images. However, any other suitable method of obtaining and identifying the unique identifier can be used.

The imaging hardware is preferably controlled by a processor running imaging software, wherein the processor preferably controls stage motion, microscope focus, and image capture, and can additionally control other functions. Imaging hardware control is preferably based on an image taken by the image hardware, but can alternatively be based on signals received from sensors or other portions of the integrated platform 30.

As a person skilled in the art will recognize from the previous detailed description and from the figures and claims, modifications and changes can be made to the preferred embodiments of the invention without departing from the scope of this invention defined in the following claims.

We claim:

1. A system for capturing particles in single-particle format, comprising:
   a plurality of pores, each pore in the plurality of pores displaced from at least one other pore in the plurality of pores and comprising:
   a chamber having an upstream end and a pore channel, fluidly coupled to the chamber at a downstream end of the chamber, and having a pore channel width configured to block particle egress, wherein adjacent chambers of the plurality of pores are separated by at least one barrier configured to block fluid flow in a direction parallel to fluid flow through their pore channels;
   an inlet channel directly fluidly coupled to the upstream end of each chamber of the plurality of pores; and
   an outlet channel directly fluidly coupled to each pore channel of the plurality of pores, wherein flow from the inlet channel is configured to reach the outlet channel only by way of the plurality of pores.

2. The system of claim 1, further comprising a second array having a second plurality of pores, a second inlet channel directly fluidly coupled to the second array, and a second outlet channel directly fluidly coupled to the second inlet channel only by way of the second plurality of parallel pores.

3. The system of claim 2, further comprising a feeder channel that couples the inlet channel and the second inlet channel in parallel.

4. The system of claim 1, wherein fluid coupling between the inlet channel and the outlet channel of the array, only by way of the plurality of pores, provides a volumetric fluid flow rate within inlet channel that is substantially equal to the volumetric fluid flow rate within the outlet channel.

5. The system of claim 1, wherein each of the plurality of pores has a non-constant cross section along its flow axis.

6. The system of claim 1, wherein the pore channel widths of successive pores of the plurality of pores decrease along a flow direction through the inlet channel.

7. The system of claim 1, wherein the inlet channel is partially defined by a self-sealing wall at least at one end of the inlet channel.

8. The system of claim 7, further including a particle removal tool operable to penetrate the self-sealing wall and to retrieve a captured particle from one of the plurality of pores.

9. The system of claim 1, further comprising a capillary particle removal unit operable to retrieve a captured particle from one of the plurality of pores.

10. The system of claim 1, further including:
    an inlet manifold, defined on the broad face of the substrate, fluidly coupled to the inlet channel of the array; and
    an outlet manifold, defined on the broad face of the substrate, fluidly coupled to the outlet channel of the array.

11. A method for capturing particles, comprising:
    providing a plurality of pores, each pore in the plurality of pores displaced from at least one other pore in the plurality of pores and comprising: a chamber having an upstream end, and a pore channel, fluidly coupled to the chamber at a downstream end of the chamber, having a pore channel width configured to block egress of a particle, wherein adjacent chambers of the plurality of pores are separated by at least one barrier configured to substantially block fluid flow in a direction parallel to fluid flow through the pore channels; an inlet channel directly fluidly coupled to the upstream end of each chamber of the plurality of pores; and an outlet channel directly fluidly coupled to each pore channel of the plurality of pores, wherein flow from the inlet channel is configured to reach the outlet channel only by way of the plurality of parallel pores; and
    delivering a sample of particles through the inlet channel, into the plurality of pores, and allowing fluid flow from the plurality of pores through the outlet channel, thereby capturing particles in single-particle format.

12. The method of claim 11, wherein the particles comprise circulating tumor cells (CTCs).

13. The method of claim 11, wherein the particles comprise circulating stem cells (CSCs).

14. The method of claim 11, wherein providing the plurality of pores comprises providing the plurality of pores at a broad face of a substrate.

15. The method of claim 14, further comprising receiving a particle removal tool into at least one of the plurality of pores, the cell removal tool providing a capillary effect that draws at least one particle into the particle removal tool.

16. The method of claim 11, further comprising backflowing fluid through the outlet channel toward the inlet channel, thereby releasing captured particles.

17. The method of claim 11, further comprising providing a second array having a second plurality of pores, a second inlet channel directly fluidly coupled to the second array, and a second outlet channel directly fluidly coupled to the second inlet channel only by way of the second plurality of parallel pores.

18. The method of claim 17, further comprising providing a feeder channel directly coupled to the inlet channel and the second inlet channel, and delivering a volume of particles into the feeder channel, thereby delivering particles into the inlet channel and the second inlet channel in parallel.

19. The method of claim 11, further comprising introducing an isolating material in the plurality of pores, thereby trapping captured particles at the plurality of pores.

20. The method of claim 19, further including transitioning the isolating material from a flow state to a set state and processing captured particles at the plurality of pores with a process reagent upon introducing the process reagent into the plurality of pores.

* * * * *

UNITED STATES PATENT AND TRADEMARK OFFICE
CERTIFICATE OF CORRECTION

PATENT NO. : 10,345,219 B2
APPLICATION NO. : 15/657553
DATED : July 9, 2019
INVENTOR(S) : Kalyan Handique et al.

It is certified that error appears in the above-identified patent and that said Letters Patent is hereby corrected as shown below:

In the Claims

Column 30, Line 7:
In Claim 11, after "comprising:", insert --¶--

Column 30, Line 14:
In Claim 11, after "channels;", insert --¶--

Column 30, Line 16:
In Claim 11, after "and", insert --¶--

Signed and Sealed this
Twenty-fifth Day of February, 2020

Andrei Iancu
*Director of the United States Patent and Trademark Office*